US007524936B2

(12) United States Patent
Lambeth et al.

(10) Patent No.: US 7,524,936 B2
(45) Date of Patent: Apr. 28, 2009

(54) MITOGENIC OXYGENASE REGULATORS

(75) Inventors: J. David Lambeth, Decatur, GA (US); Guangjie Chang, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 11/712,222

(22) Filed: Feb. 27, 2007

(65) Prior Publication Data

US 2007/0190576 A1 Aug. 16, 2007

Related U.S. Application Data

(60) Division of application No. 10/850,060, filed on May 20, 2004, now Pat. No. 7,202,052, which is a continuation of application No. 09/999,248, filed on Nov. 15, 2001, now Pat. No. 6,846,672.

(60) Provisional application No. 60/289,172, filed on May 7, 2001, provisional application No. 60/289,537, filed on May 7, 2001, provisional application No. 60/251,364, filed on Dec. 5, 2000, provisional application No. 60/249,305, filed on Nov. 16, 2000.

(51) Int. Cl.
*G01N 33/53* (2006.01)
*G01N 33/573* (2006.01)
*C07K 16/18* (2006.01)
*C07K 16/40* (2006.01)

(52) U.S. Cl. .............................. 530/387.1; 530/388.26; 530/389.1; 530/391.3; 435/7.1; 435/7.2; 435/7.4

(58) Field of Classification Search ........................ None
See application file for complete search history.

(56) References Cited

U.S. PATENT DOCUMENTS

2002/0022022 A1 2/2002 Shi et al.

FOREIGN PATENT DOCUMENTS

| WO | WO 00/28031 | 5/2000 |
|---|---|---|
| WO | WO 01/53312 | 7/2001 |
| WO | WO 01/79467 | 10/2001 |

OTHER PUBLICATIONS

Brenner, SE et al. Proc. Natl. Acad. Sci. USA (1998) 95:6073-6078.*
Banfi, B. et al. "A Ca(2+)-Activated NADPH Oxidase in Testis, Spleen, and Lymph Nodes", Journal of Biological Chemistry, United States, Oct. 5, 2001, vol. 276, No. 40, pp. 37594-37601.
Biberstine-Kinkade, K., et al., "Mutagenesis of an Arginie- and Lysine-rich Domain in the gp91$^{phox}$ Subunit of the Phagocyte NADPH-oxidase Flavocytochrome $b_{558}$," *J. Biol. Chem.*, vol. 274, No. 15, pp. 10451-10457 (1999).
Bjiorgvinsdottir et al., "Cloning of murine gp91 (phox) and functional expression in a human X-liked . . ." Blood, 87 (5), 2005-2010 (1996).
Burdon, R. H., "Superoxide and Hydrogen Peroxide in Relation to Mammalian Cell Proliferation," *Free Radical Biol. Med.*, vol. 18, No. 4, pp. 775-794 (1995).

Cheng Guangjie et al. Homologs of Gp91phox: Cloning and Tissue Expression of Nox3, Nox4 and Nox5, Gene (Amsterdam), vol. 269, No. 1-2, 23001, pp. 131-140.
Cheng G. et al., "NADPH Oxidase 4 (NOX4), a Homolog of gp91 and Mox1 (NOX1)", May 10, 2000.
Church, S. L., et al., "Increased Manganese Superoxide Dismutase Expression Suppresses the Malignant Phenotype of Human Melanoma Cells," *Proc. Natl. Acad. Sci. USA*, vol. 90, pp. 3113-3117 (1993).
Emmendörffer, A., et al., "Production of Oxygen Radicals By Fibroblasts and Neutrophils from a Patient with X-Linked Chronic Granulomatous Disease," *Eur. J. Haematol*, vol. 51, pp. 223-227 (1993).
Fernandez-Pol, J.A., et al., "Correlation Between the Loss of the Transformed Phenotype and an Increase in Superoxide Dismutase Activity in a Revertant Subclone of Sarcoma Virus-infected Mammalian Cells," *Can. Res.*, vol. 42, pp. 609-617 (1982).
Fukui, T., et al., "p22phox mRNA Expression and NADPH Oxidase Activity are Increased in Aortas from Hypertensive Rats," *Cir. Res.*, vol. 80, No. 1, pp. 45-51, (1997).
Gardner, P. R., et al., "Superoxide Radical and Iron Modulate Aconitase Activity in Mammalian Cells," *J. Biol. Chem.*, vol. 270, No. 22, pp. 13399-13405 (1995).
Geiszt, M., et al., "Identification of Renox, an NAD(P)H Oxidase in Kidney," *PNAS*, vol. 97, No. 14, pp. 8010-8014 (2000).
Griendling, K. K., et al., "Angiotensin II Stimulates NADH and NADPH Oxidase Activity in Cultured Vascular Smooth Muscle Cells," *Cir. Res.*, vol. 74, No. 6, pp. 1141-1148 (1994).
Irani, K., et al., "Mitogenic Signaling Mediated by Oxidants in Ras-Transformed Fibroblasts," *Science*, vol. 275, No. 5306, pp. 1649-1652 (1997).
Isogai, Y., "Superoxide-producing Cytochrome *b*: Enzymatic and Electron Paramagnetic Resonance Properties of Cytochrome $b_{558}$ Purified from Neutrophils," *J. Biol. Chem.*, vol. 268, No. 6, pp. 4025-4031 (1993).
Kikuchi, H., et al., "NADPH Oxidase Subunit, pg91$^{phox}$ Homologue, Preferentially Expressed in Human Colon Epithelial Cells," *Gene*, vol. 254, pp. 237-243 (2000).
Lambeth, J.D., et al., "Novel Homologs of gp91*phox*," *Trends in Biochemical Sciences*, vol. 25, pp. 459-461 (2000).
Lambeth, J.D., "Regulation of the Phagocyte Respiratory Burst Oxidase by Protein Interactions," *Journal of Biochemistry and Molecular Biology*, vol. 33, No. 6, pp. 427-439 (2000).
Lloyd, D., "Human DNA Sequence from Clone 146H21 on Chromosome Xq22", Jan. 10, 1997.
Mastsubara, T., et al., "Increased Superoxide Anion Release from Human Endothelial Cells in Response to Cytokines," *J. Immun.*, vol. 137, No. 10, pp. 3295-3298 (1986).

(Continued)

*Primary Examiner*—Eileen B O'Hara
*Assistant Examiner*—F. Pierre VanderVegt
(74) *Attorney, Agent, or Firm*—Klarquist Sparkman, LLP

(57) ABSTRACT

The present invention relates to new genes encoding for the production of novel nox enzyme proteins involved in generation of reactive oxygen intermediates that affect cell division. The present invention also provides vectors containing these genes, cells transfected with these vectors, antibodies raised against these novel proteins, kits for detection, localization and measurement of these genes and proteins, and methods to determine the activity of drugs to affect the activity of the proteins of the present invention.

12 Claims, 10 Drawing Sheets

OTHER PUBLICATIONS

Meier, B., et al., "Human Fibroblasts Release Reactive Oxygen Species in Response to Interleukin-1 or Tumor Necrosis Factor-α," *Biochem. J.*, vol. 263, No. 2, pp. 539-545 (1989).

Merta, A. et al., "The Rat S-Adenosylhomocysteine Hydrolase Promoter", Biochemical and Biophysical Research Communications, United States, Nov. 26, 1997, vol. 240, No. 3, pp. 580-585.

Pagano, P. J., et al., "Localization of a Constitutively Active, Phagocyte-like NADPH Oxidase in Rabbit Aortic Adventitia: Enhancement by Angiotensin II," *Proc. Natl. Acad. Sci. USA*, vol. 94, No. 26, pp. 14483-14488 (1997).

Pepe, G.J. et al. "Cloning of the 11Beta Hydroxysteroid Dehydrogenase (11Beta-HSD)—2 Gene in the Baboon: Effects of Estradiol on Promoter Activity of 11Beta-HSD-1 and -2 in Placental JEG-3 Cells", U.S. National Library of Medicine, Jan. 18, 1999.

Schmidt, K. N., et al., "The Roles of Hydrogen Peroxide and Superoxide as Messengers in the Activation of Transcription Factor NF-κB," *Chem. & Bio.*, vol. 2, No. 1, pp. 13-22 (1995).

Schreck, R., et al., "Reactive Oxygen Intermediates as Apparently Widely Used Messengers in the Activation of the NF-κB Transcription Factor and HIV-1," *EMBO J.*, vol. 10, No. 8, pp. 2247-2258 (1991).

Shiose, A., et al., "A Novel Superoxidase-producing NAD(P)H Oxidase in Kidney", *J. Biol. Chem.*, vol. 276, No. 2, pp. 1417-1423 (2001).

Sugano, S. et al., "NEDO Human cDNA Sequencing Project", Sep. 29, 2000.

Suh, Y., et al., "Cell Transformation by the Superoxide-Generating Oxidase Mox1," *Nature*, vol. 401, No. 6748, pp. 79-82 (1999).

Sundaresan, M., et al., "Requirement for Generation of $H_2O_2$ for Platelet-Derived Growth Factor Signal Transduction," *Science*, vol. 270, pp. 296-299 (1995).

Szatrowski, T.P., et al., "Production of Large Amounts of Hydrogen Peroxide by Human Tumor Cells," *Canc. Res.*, vol. 51, No. 3, pp. 794-798 (1991).

Uhlinger, D.J., "Nucleoside Triphosphate Requirements for Superoxide Generation and Phosphorylation in a Cell-Free System from Human Neutrophils," *J. Biol. Chem.*, vol. 266, No. 31, pp. 20990-20997 (1991).

Ushio-Fukai M., et al., "$p22^{phox}$ is a Critical Component of the Superoxide-Generating NADH/NADPH Oxidase System and Regulates Angiotensin II-Induced Hypertrophy in Vascular Smooth Muscle Cells," *J. Biol. Chem*, vol. 271, No. 38, pp. 23317-23321 (1996).

Yan, T., et al., "Manganese-Containing Superoxide Dismutase Overexpression Causes Phenotypic Reversion in SV40-Transformed Human Lung Fibroblasts," *Canc. Res.*, vol. 56, pp. 2864-2871 (1996).

Yu, L., et al., "Biosynthesis of the Phagocyte NADPH Oxidase Cytochrome $b_{588}$: Role of Heme Incorporation and Heterodimer Formation in Maturation and Stability of $gp91^{phox}$ and $p22^{phox}$ Subunits," *J. Biol. Chem*, vol. 272, No. 43, pp. 27288-27294 (1997).

Genbank Accession No. AF254621, May 9, 2001, (2 pages).
Genbank Accession No. AAG33638, Sep. 6, 2005, (2 pages).
Genbank Accession No. AF317889, Sep. 6, 2005, (2 pages).
Genbank Accession No. BAB15319, Sep. 12, 2006, (2 pages).
Genbank Accession No. AK026011, Sep. 12, 2006, (2 pages).

* cited by examiner

SEQUENCE LISTING

<160> NUMBER OF SEQ ID NOS: 34

<210> SEQ ID NO 1
<211> LENGTH: 2232

```
<212> TYPE: DNA
<213> ORGANISM: Homo sapiens
<220> FEATURE:
<221> NAME/KEY: CDS
<222> LOCATION: (87)..(1823)

<400> SEQUENCE: 1
ccgcacaact gtaaccgctg ccccggccgc cgcccgctcc ttctcgggcc ggcgggcaca        60
gagcgcagcg cggcggggcc ggcggc atg gct gtg tcc tgg agg agc tgg ctc       113
                              Met Ala Val Ser Trp Arg Ser Trp Leu
                                1               5 gcc aac gaa ggg gtt aaa cac ctc tgc ctg ttc atc tgg ctc tcc atg       161
Ala Asn Glu Gly Val Lys His Leu Cys Leu Phe Ile Trp Leu Ser Met
 10              15                  20                  25 aat gtc ctg ctt ttc tgg aaa acc ttc ttg ctg tat aac caa ggg cca       209
Asn Val Leu Leu Phe Trp Lys Thr Phe Leu Leu Tyr Asn Gln Gly Pro
             30                  35                  40 gag tat cac tac ctc cac cag atg ttg ggg cta gga ttg tgt cta agc       257
Glu Tyr His Tyr Leu His Gln Met Leu Gly Leu Gly Leu Cys Leu Ser
         45                  50                  55 aga gcc tca gca tct gtt ctt aac ctc aac tgc agc ctt atc ctt tta       305
Arg Ala Ser Ala Ser Val Leu Asn Leu Asn Cys Ser Leu Ile Leu Leu
     60                  65                  70 ccc atg tgc cga aca ctc ttg gct tac ctc cga gga tca cag aag gtt       353
Pro Met Cys Arg Thr Leu Leu Ala Tyr Leu Arg Gly Ser Gln Lys Val
 75                  80                  85 cca agc agg aga acc agg aga ttg ttg gat aaa agc aga aca ttc cat       401
Pro Ser Arg Arg Thr Arg Arg Leu Leu Asp Lys Ser Arg Thr Phe His
 90                  95                 100                 105 att acc tgt ggt gtt act atc tgt att ttc tca ggc gtg cat gtg gct       449
Ile Thr Cys Gly Val Thr Ile Cys Ile Phe Ser Gly Val His Val Ala
             110                 115                 120 gcc cat ctg gtg aat gcc ctc aac ttc tca gtg aat tac agt gaa gac       497
Ala His Leu Val Asn Ala Leu Asn Phe Ser Val Asn Tyr Ser Glu Asp
         125                 130                 135 ttt gtt gaa ctg aat gca gca aga tac cga gat gag gat cct aga aaa       545
Phe Val Glu Leu Asn Ala Ala Arg Tyr Arg Asp Glu Asp Pro Arg Lys
     140                 145                 150 ctt ctc ttc aca act gtt cct ggc ctg aca ggg gtc tgc atg gtg gtg       593
Leu Leu Phe Thr Thr Val Pro Gly Leu Thr Gly Val Cys Met Val Val
 155                 160                 165 gtg cta ttc ctc atg atc aca gcc tct aca tat gca ata aga gtt tct       641
Val Leu Phe Leu Met Ile Thr Ala Ser Thr Tyr Ala Ile Arg Val Ser
 170                 175                 180                 185 aac tat gat atc ttc tgg tat act cat aac ctc ttc ttt gtc ttc tac       689
Asn Tyr Asp Ile Phe Trp Tyr Thr His Asn Leu Phe Phe Val Phe Tyr
             190                 195                 200 atg ctg ctg acg ttg cat gtt tca gga ggg ctg ctg aag tat caa act       737
Met Leu Leu Thr Leu His Val Ser Gly Gly Leu Leu Lys Tyr Gln Thr
         205                 210                 215 aat tta gat acc cac cct ccc ggc tgc atc agt ctt aac cga acc agc       785
Asn Leu Asp Thr His Pro Pro Gly Cys Ile Ser Leu Asn Arg Thr Ser
     220                 225                 230 tct cag aat att tcc tta cca gag tat ttc tca gaa cat ttt cat gaa       833
Ser Gln Asn Ile Ser Leu Pro Glu Tyr Phe Ser Glu His Phe His Glu
 235                 240                 245 cct ttc cct gaa gga ttt tca aaa ccg gca gag ttt acc cag cac aaa       881
Pro Phe Pro Glu Gly Phe Ser Lys Pro Ala Glu Phe Thr Gln His Lys
 250                 255                 260                 265 ttt gtg aag att tgt atg gaa gag ccc aga ttc caa gct aat ttt cca       929
```

|  |  |
|---|---|
| Phe Val Lys Ile Cys Met Glu Glu Pro Arg Phe Gln Ala Asn Phe Pro<br>     270        275       280 | |
| cag act tgg ctt tgg att tct gga cct ttg tgc ctg tac tgt gcc gaa<br>Gln Thr Trp Leu Trp Ile Ser Gly Pro Leu Cys Leu Tyr Cys Ala Glu<br>     285        290       295 | 977 |
| aga ctt tac agg tat atc cgg agc aat aag cca gtc acc atc att tcg<br>Arg Leu Tyr Arg Tyr Ile Arg Ser Asn Lys Pro Val Thr Ile Ile Ser<br>     300        305       310 | 1025 |
| gtc ata agt cat ccc tca gat gtc atg gaa atc cga atg gtc aaa gaa<br>Val Ile Ser His Pro Ser Asp Val Met Glu Ile Arg Met Val Lys Glu<br>     315        320       325 | 1073 |
| aat ttt aaa gca aga cct ggt cag tat att act cta cat tgt ccc agt<br>Asn Phe Lys Ala Arg Pro Gly Gln Tyr Ile Thr Leu His Cys Pro Ser<br>330        335        340       345 | 1121 |
| gta tct gca tta gaa aat cat cca ttt acc ctc aca atg tgt cca act<br>Val Ser Ala Leu Glu Asn His Pro Phe Thr Leu Thr Met Cys Pro Thr<br>        350        355       360 | 1169 |
| gaa acc aaa gca aca ttt ggg gtt cat ctt aaa ata gta gga gac tgg<br>Glu Thr Lys Ala Thr Phe Gly Val His Leu Lys Ile Val Gly Asp Trp<br>     365        370       375 | 1217 |
| aca gaa cga ttt cga gat tta cta ctg cct cca tct agt caa gac tcc<br>Thr Glu Arg Phe Arg Asp Leu Leu Leu Pro Pro Ser Ser Gln Asp Ser<br>     380        385       390 | 1265 |
| gaa att ctg ccc ttc att caa tct aga aat tat ccc aag ctg tat att<br>Glu Ile Leu Pro Phe Ile Gln Ser Arg Asn Tyr Pro Lys Leu Tyr Ile<br>     395        400       405 | 1313 |
| gat ggt cct ttt gga agt cca ttt gag gaa tca ctg aac tat gag gtc<br>Asp Gly Pro Phe Gly Ser Pro Phe Glu Glu Ser Leu Asn Tyr Glu Val<br>410        415        420       425 | 1361 |
| agc ctc tgc gtg gct gga ggc att gga gta act cca ttt gca tca ata<br>Ser Leu Cys Val Ala Gly Gly Ile Gly Val Thr Pro Phe Ala Ser Ile<br>        430        435       440 | 1409 |
| ctc aac acc ctg ttg gat gac tgg aaa cca tac aag ctt aga aga cta<br>Leu Asn Thr Leu Leu Asp Asp Trp Lys Pro Tyr Lys Leu Arg Arg Leu<br>     445        450       455 | 1457 |
| tac ttt att tgg gta tgc aga gat atc cag tcc ttc cgt tgg ttt gca<br>Tyr Phe Ile Trp Val Cys Arg Asp Ile Gln Ser Phe Arg Trp Phe Ala<br>        460        465       470 | 1505 |
| gat tta ctc tgt atg ttg cat aac aag ttt tgg caa gag aac aga cct<br>Asp Leu Leu Cys Met Leu His Asn Lys Phe Trp Gln Glu Asn Arg Pro<br>     475        480       485 | 1553 |
| gac tat gtc aac atc cag ctg tac ctc agt caa aca gat ggg ata cag<br>Asp Tyr Val Asn Ile Gln Leu Tyr Leu Ser Gln Thr Asp Gly Ile Gln<br>490        495        500       505 | 1601 |
| aag ata att gga gaa aaa tat cat gca ctg aat tca aga ctg ttt ata<br>Lys Ile Ile Gly Glu Lys Tyr His Ala Leu Asn Ser Arg Leu Phe Ile<br>        510        515       520 | 1649 |
| gga cgt cct cgg tgg aaa ctt ttg ttt gat gaa ata gca aaa tat aac<br>Gly Arg Pro Arg Trp Lys Leu Leu Phe Asp Glu Ile Ala Lys Tyr Asn<br>     525        530       535 | 1697 |
| aga gga aaa aca gtt ggt gtt ttc tgt tgt gga ccc aat tca cta tcc<br>Arg Gly Lys Thr Val Gly Val Phe Cys Cys Gly Pro Asn Ser Leu Ser<br>        540        545       550 | 1745 |
| aag act ctt cat aaa ctg agt aac cag aac aac tca tat ggg aca aga<br>Lys Thr Leu His Lys Leu Ser Asn Gln Asn Asn Ser Tyr Gly Thr Arg<br>     555        560       565 | 1793 |
| ttt gaa tac aat aaa gag tct ttc agc tga aaacttttgc catgaagcag<br>Phe Glu Tyr Asn Lys Glu Ser Phe Ser<br>570        575 | 1843 |

```
gactctaaag aaggaatgag tgcaatttct aagactttga aactcagcgg aatcaatcag    1903
ctgtgttatg ccaaagaata gtaaggtttt cttatttatg attatttgaa aatggaaatg    1963
tgagaatgtg gcaacatgac cgtcacatta catgtttaat ctggaaacca aagagaccct    2023
gaagaatatt tgatgtgatg attcattttc agttctcaaa ttaaaagaaa actgttagat    2083
gcacactgtt gattttcatg gtggattcaa gaactcccta gtgaggagct gaacttgctc    2143
aatctaaggc tgattgtcgt gttcctcttt aaattgtttt tggttgaaca aatgcaagat    2203
tgaacaaaat taaaaattca ttgaagctg                                      2232
```

<210> SEQ ID NO 2
<211> LENGTH: 578
<212> TYPE: PRT
<213> ORGANISM: Homo sapiens

<400> SEQUENCE: 2

```
Met Ala Val Ser Trp Arg Ser Trp Leu Ala Asn Glu Gly Val Lys His
 1               5                  10                  15

Leu Cys Leu Phe Ile Trp Leu Ser Met Asn Val Leu Leu Phe Trp Lys
                20                  25                  30

Thr Phe Leu Leu Tyr Asn Gln Gly Pro Glu Tyr His Tyr Leu His Gln
         35                  40                  45

Met Leu Gly Leu Gly Leu Cys Leu Ser Arg Ala Ser Ala Ser Val Leu
     50                  55                  60

Asn Leu Asn Cys Ser Leu Ile Leu Pro Met Cys Arg Thr Leu Leu
 65                  70                  75                  80

Ala Tyr Leu Arg Gly Ser Gln Lys Val Pro Ser Arg Thr Arg Arg
                 85                  90                  95

Leu Leu Asp Lys Ser Arg Thr Phe His Ile Thr Cys Gly Val Thr Ile
                100                 105                 110

Cys Ile Phe Ser Gly Val His Val Ala His Leu Val Asn Ala Leu
            115                 120                 125

Asn Phe Ser Val Asn Tyr Ser Glu Asp Phe Val Glu Leu Asn Ala Ala
    130                 135                 140

Arg Tyr Arg Asp Glu Asp Pro Arg Lys Leu Leu Phe Thr Thr Val Pro
145                 150                 155                 160

Gly Leu Thr Gly Val Cys Met Val Val Leu Phe Leu Met Ile Thr
                165                 170                 175

Ala Ser Thr Tyr Ala Ile Arg Val Ser Asn Tyr Asp Ile Phe Trp Tyr
            180                 185                 190

Thr His Asn Leu Phe Phe Val Phe Tyr Met Leu Leu Thr Leu His Val
        195                 200                 205

Ser Gly Gly Leu Leu Lys Tyr Gln Thr Asn Leu Asp Thr His Pro Pro
    210                 215                 220

Gly Cys Ile Ser Leu Asn Arg Thr Ser Ser Gln Asn Ile Ser Leu Pro
225                 230                 235                 240

Glu Tyr Phe Ser Glu His Phe His Glu Pro Phe Pro Glu Gly Phe Ser
                245                 250                 255

Lys Pro Ala Glu Phe Thr Gln His Lys Phe Val Lys Ile Cys Met Glu
            260                 265                 270

Glu Pro Arg Phe Gln Ala Asn Phe Pro Gln Thr Trp Leu Trp Ile Ser
        275                 280                 285

Gly Pro Leu Cys Leu Tyr Cys Ala Glu Arg Leu Tyr Arg Tyr Ile Arg
    290                 295                 300
```

-continued

```
Ser Asn Lys Pro Val Thr Ile Ile Ser Val Ile Ser His Pro Ser Asp
305                 310                 315                 320

Val Met Glu Ile Arg Met Val Lys Glu Asn Phe Lys Ala Arg Pro Gly
            325                 330                 335

Gln Tyr Ile Thr Leu His Cys Pro Ser Val Ser Ala Leu Glu Asn His
        340                 345                 350

Pro Phe Thr Leu Thr Met Cys Pro Thr Glu Thr Lys Ala Thr Phe Gly
    355                 360                 365

Val His Leu Lys Ile Val Gly Asp Trp Thr Glu Arg Phe Arg Asp Leu
370                 375                 380

Leu Leu Pro Pro Ser Ser Gln Asp Ser Glu Ile Leu Pro Phe Ile Gln
385                 390                 395                 400

Ser Arg Asn Tyr Pro Lys Leu Tyr Ile Asp Gly Pro Phe Gly Ser Pro
            405                 410                 415

Phe Glu Glu Ser Leu Asn Tyr Glu Val Ser Leu Cys Val Ala Gly Gly
        420                 425                 430

Ile Gly Val Thr Pro Phe Ala Ser Ile Leu Asn Thr Leu Leu Asp Asp
    435                 440                 445

Trp Lys Pro Tyr Lys Leu Arg Arg Leu Tyr Phe Ile Trp Val Cys Arg
450                 455                 460

Asp Ile Gln Ser Phe Arg Trp Phe Ala Asp Leu Leu Cys Met Leu His
465                 470                 475                 480

Asn Lys Phe Trp Gln Glu Asn Arg Pro Asp Tyr Val Asn Ile Gln Leu
            485                 490                 495

Tyr Leu Ser Gln Thr Asp Gly Ile Gln Lys Ile Ile Gly Glu Lys Tyr
        500                 505                 510

His Ala Leu Asn Ser Arg Leu Phe Ile Gly Arg Pro Arg Trp Lys Leu
    515                 520                 525

Leu Phe Asp Glu Ile Ala Lys Tyr Asn Arg Gly Lys Thr Val Gly Val
530                 535                 540

Phe Cys Cys Gly Pro Asn Ser Leu Ser Lys Thr Leu His Lys Leu Ser
545                 550                 555                 560

Asn Gln Asn Asn Ser Tyr Gly Thr Arg Phe Glu Tyr Asn Lys Glu Ser
            565                 570                 575

Phe Ser
```

```
<210> SEQ ID NO 3
<211> LENGTH: 2223
<212> TYPE: DNA
<213> ORGANISM: Homo sapiens
<220> FEATURE:
<221> NAME/KEY: CDS
<222> LOCATION: (73)..(1770)

<400> SEQUENCE: 3
gccgacgcgg acggcaacgg ggccatcacc ttcgaggagc tccgggacga gctgcagcgc    60
ttccccggag tc atg gag aac ctg acc atc agc act gcc cac tgg ctg acg   111
              Met Glu Asn Leu Thr Ile Ser Thr Ala His Trp Leu Thr
                1               5                   10 gcc ccc gcc ccc cgc cca cgc ccg cgc cgg ccg cgc cag ctg acc cgc   159
Ala Pro Ala Pro Arg Pro Arg Pro Arg Arg Pro Arg Gln Leu Thr Arg
 15                  20                  25 gcc tac tgg cac aac cac cgc agc cag ctg ttc tgc ctg gcc acc tat   207
Ala Tyr Trp His Asn His Arg Ser Gln Leu Phe Cys Leu Ala Thr Tyr
 30                  35                  40                  45 gca ggc ctc cac gtg ctg ctc ttc ggg ctg gcg gcc agc gcg cac cgg   255
```

-continued

```
                Ala Gly Leu His Val Leu Leu Phe Gly Leu Ala Ala Ser Ala His Arg
                             50                  55                  60 gac ctc ggc gcc agc gtc atg gtg gcc aag ggc tgt ggc cag tgc ctc                    303
Asp Leu Gly Ala Ser Val Met Val Ala Lys Gly Cys Gly Gln Cys Leu
             65                  70                  75 aac ttc gac tgc agc ttc atc gcg gtg ctg atg ctc aga cgc tgc ctc                    351
Asn Phe Asp Cys Ser Phe Ile Ala Val Leu Met Leu Arg Arg Cys Leu
         80                  85                  90 acc tgg ctg cgg gcc acg tgg ctg gct caa gtc cta cca ctg gac cag                    399
Thr Trp Leu Arg Ala Thr Trp Leu Ala Gln Val Leu Pro Leu Asp Gln
     95                 100                 105 aac atc cag ttc cac cag ctt atg ggc tac gtg gta gtg ggg ctg tcc                    447
Asn Ile Gln Phe His Gln Leu Met Gly Tyr Val Val Val Gly Leu Ser
110                 115                 120                 125 ctc gtg cac act gtg gct cac act gtg aac ttt gta ctc cag gct cag                    495
Leu Val His Thr Val Ala His Thr Val Asn Phe Val Leu Gln Ala Gln
                130                 135                 140 gcg gag gcc agc cct ttc cag ttc tgg gag ctg ctc acc acg agg                        543
Ala Glu Ala Ser Pro Phe Gln Phe Trp Glu Leu Leu Leu Thr Thr Arg
            145                 150                 155 cct ggc att ggc tgg gta cac ggt tcg gcc tcc ccg aca ggt gtc gct                    591
Pro Gly Ile Gly Trp Val His Gly Ser Ala Ser Pro Thr Gly Val Ala
        160                 165                 170 ctg ctg ctg ctc ctc ctc atg ttc atc tgc tcc agt tcc tgc atc                        639
Leu Leu Leu Leu Leu Leu Met Phe Ile Cys Ser Ser Ser Cys Ile
    175                 180                 185 cgc agg agt ggc cac ttt gag gtg ttc tat tgg act cac ctg tcc tac                    687
Arg Arg Ser Gly His Phe Glu Val Phe Tyr Trp Thr His Leu Ser Tyr
190                 195                 200                 205 ctc ctc gtg tgg ctt ctg ctc atc ttt cat ggg ccc aac ttc tgg aag                    735
Leu Leu Val Trp Leu Leu Leu Ile Phe His Gly Pro Asn Phe Trp Lys
                210                 215                 220 tgg ctg ctg gtg cct gga atc ttg ttt ttc ctg gag aag gcc atc gga                    783
Trp Leu Leu Val Pro Gly Ile Leu Phe Phe Leu Glu Lys Ala Ile Gly
            225                 230                 235 ctg gca gtg tcc cgc atg gca gcc gtg tgc atc atg gaa gtc aac ctc                    831
Leu Ala Val Ser Arg Met Ala Ala Val Cys Ile Met Glu Val Asn Leu
        240                 245                 250 ctc ccc tcc aag gtc act cat ctc ctc atc aag cgg ccc cct ttt ttt                    879
Leu Pro Ser Lys Val Thr His Leu Leu Ile Lys Arg Pro Pro Phe Phe
    255                 260                 265 cac tat aga cct ggt gac tac ttg tat ctg aac atc ccc acc att gct                    927
His Tyr Arg Pro Gly Asp Tyr Leu Tyr Leu Asn Ile Pro Thr Ile Ala
270                 275                 280                 285 cgc tat gag tgg cac ccc ttc acc atc agc agt gct cct gag cag aaa                    975
Arg Tyr Glu Trp His Pro Phe Thr Ile Ser Ser Ala Pro Glu Gln Lys
                290                 295                 300 gac act atc tgg ctg cac att cgg tcc caa ggc cag tgg aca aac agg                   1023
Asp Thr Ile Trp Leu His Ile Arg Ser Gln Gly Gln Trp Thr Asn Arg
            305                 310                 315 ctg tat gag tcc ttc aag gca tca gac cca ctg ggc cgt ggt tct aag                   1071
Leu Tyr Glu Ser Phe Lys Ala Ser Asp Pro Leu Gly Arg Gly Ser Lys
        320                 325                 330 agg ctg tcg agg agt gtg aca atg aga aag agt caa agg tcg tcc aag                   1119
Arg Leu Ser Arg Ser Val Thr Met Arg Lys Ser Gln Arg Ser Ser Lys
    335                 340                 345 ggc tct gag ata ctt ttg gag aaa cac aaa ttc tgt aac atc aag tgc                   1167
Gly Ser Glu Ile Leu Leu Glu Lys His Lys Phe Cys Asn Ile Lys Cys
350                 355                 360                 365
```

-continued

```
tac atc gat ggg cct tat ggg acc ccc acc cgc agg atc ttt gcc tct      1215
Tyr Ile Asp Gly Pro Tyr Gly Thr Pro Thr Arg Arg Ile Phe Ala Ser
            370                 375                 380 gag cat gcc gtg ctc atc ggg gca ggc atc ggc atc acc ccc ttt gct      1263
Glu His Ala Val Leu Ile Gly Ala Gly Ile Gly Ile Thr Pro Phe Ala
        385                 390                 395 tcc att ctg cag agt atc atg tac agg cac cag aaa aga aag cat act      1311
Ser Ile Leu Gln Ser Ile Met Tyr Arg His Gln Lys Arg Lys His Thr
    400                 405                 410 tgc ccc agc tgc cag cac tcc tgg atc gaa ggt gtc caa gac aac atg      1359
Cys Pro Ser Cys Gln His Ser Trp Ile Glu Gly Val Gln Asp Asn Met
415                 420                 425 aag ctc cat aag gtg gac ttt atc tgg atc aac aga gac cag cgg tct      1407
Lys Leu His Lys Val Asp Phe Ile Trp Ile Asn Arg Asp Gln Arg Ser
430                 435                 440                 445 ttc gag tgg ttt gtg agc ctg ctg act aaa ctg gag atg gac cag gcc      1455
Phe Glu Trp Phe Val Ser Leu Leu Thr Lys Leu Glu Met Asp Gln Ala
                450                 455                 460 gag gag gct caa tac ggc cgc ttc ctg gag ctg cat atg tac atg aca      1503
Glu Glu Ala Gln Tyr Gly Arg Phe Leu Glu Leu His Met Tyr Met Thr
            465                 470                 475 tct gca ctg ggc aag aat gac atg aag gcc att ggc ctg cag atg gcc      1551
Ser Ala Leu Gly Lys Asn Asp Met Lys Ala Ile Gly Leu Gln Met Ala
        480                 485                 490 ctt gac ctc ctg gcc aac aag gag aag aaa gac tcc atc acg ggg ctg      1599
Leu Asp Leu Leu Ala Asn Lys Glu Lys Lys Asp Ser Ile Thr Gly Leu
    495                 500                 505 cag acg cgc acc cag cct ggg cgg cct gac tgg agc aag gtg ttc cag      1647
Gln Thr Arg Thr Gln Pro Gly Arg Pro Asp Trp Ser Lys Val Phe Gln
510                 515                 520                 525 aaa gtg gct gct gag aag aag ggc aag gtg cag gtc ttc ttc tgt ggc      1695
Lys Val Ala Ala Glu Lys Lys Gly Lys Val Gln Val Phe Phe Cys Gly
                530                 535                 540 tcc cca gct ctg gcc aag gtg ctg aag ggc cat tgt gag aag ttc ggc      1743
Ser Pro Ala Leu Ala Lys Val Leu Lys Gly His Cys Glu Lys Phe Gly
            545                 550                 555 ttc aga ttt ttc caa gag aat ttc tag cctcacctct ccaagctctg           1790
Phe Arg Phe Phe Gln Glu Asn Phe
            560                 565 ccccaagtcc acaccatggg tctgcttcat cgcattagta taaatgcccc cacagggacc    1850
agcctcagat gacccaccca ataagacaaa gcctagggac cccctaatcc tgctcaacag    1910
agagaacagg agaccccaag gggcagatga acttcctcta gaaccagggg aaggggcag     1970 tgccttgttc agtctgctgt agattctggg gtttctgtga aagtgaggga accagaggct    2030
ggtcacggga gcttggtggt ggggttcgag ggggcagagg gcaaccactc ctccaaacat    2090
tttccgacgg agccttcccc cacatccatg gtcccaaacc tgcccaatca tcacagtcat    2150
ttggaagctt atttctccgg catcttataa aattgttcaa acctacagta aaaaaaaaaa    2210
aaaaaaaaaa aaa                                                       2223

<210> SEQ ID NO 4
<211> LENGTH: 565
<212> TYPE: PRT
<213> ORGANISM: Homo sapiens

<400> SEQUENCE: 4

Met Glu Asn Leu Thr Ile Ser Thr Ala His Trp Leu Thr Ala Pro Ala
1               5                   10                  15
```

-continued

```
Pro Arg Pro Arg Pro Arg Arg Pro Arg Gln Leu Thr Arg Ala Tyr Trp
            20                  25                  30
His Asn His Arg Ser Gln Leu Phe Cys Leu Ala Thr Tyr Ala Gly Leu
        35                  40                  45
His Val Leu Leu Phe Gly Leu Ala Ala Ser Ala His Arg Asp Leu Gly
    50                  55                  60
Ala Ser Val Met Val Ala Lys Gly Cys Gly Gln Cys Leu Asn Phe Asp
65                  70                  75                  80
Cys Ser Phe Ile Ala Val Leu Met Leu Arg Arg Cys Leu Thr Trp Leu
                85                  90                  95
Arg Ala Thr Trp Leu Ala Gln Val Leu Pro Leu Asp Gln Asn Ile Gln
                100                 105                 110
Phe His Gln Leu Met Gly Tyr Val Val Val Gly Leu Ser Leu Val His
            115                 120                 125
Thr Val Ala His Thr Val Asn Phe Val Leu Gln Ala Gln Ala Glu Ala
    130                 135                 140
Ser Pro Phe Gln Phe Trp Glu Leu Leu Leu Thr Thr Arg Pro Gly Ile
145                 150                 155                 160
Gly Trp Val His Gly Ser Ala Ser Pro Thr Gly Val Ala Leu Leu Leu
                165                 170                 175
Leu Leu Leu Leu Met Phe Ile Cys Ser Ser Ser Cys Ile Arg Arg Ser
                180                 185                 190
Gly His Phe Glu Val Phe Tyr Trp Thr His Leu Ser Tyr Leu Leu Val
            195                 200                 205
Trp Leu Leu Leu Ile Phe His Gly Pro Asn Phe Trp Lys Trp Leu Leu
    210                 215                 220
Val Pro Gly Ile Leu Phe Phe Leu Glu Lys Ala Ile Gly Leu Ala Val
225                 230                 235                 240
Ser Arg Met Ala Ala Val Cys Ile Met Glu Val Asn Leu Leu Pro Ser
                245                 250                 255
Lys Val Thr His Leu Leu Ile Lys Arg Pro Pro Phe Phe His Tyr Arg
                260                 265                 270
Pro Gly Asp Tyr Leu Tyr Leu Asn Ile Pro Thr Ile Ala Arg Tyr Glu
            275                 280                 285
Trp His Pro Phe Thr Ile Ser Ser Ala Pro Glu Gln Lys Asp Thr Ile
    290                 295                 300
Trp Leu His Ile Arg Ser Gln Gly Gln Trp Thr Asn Arg Leu Tyr Glu
305                 310                 315                 320
Ser Phe Lys Ala Ser Asp Pro Leu Gly Arg Gly Ser Lys Arg Leu Ser
                325                 330                 335
Arg Ser Val Thr Met Arg Lys Ser Gln Arg Ser Ser Lys Gly Ser Glu
                340                 345                 350
Ile Leu Leu Glu Lys His Lys Phe Cys Asn Ile Lys Cys Tyr Ile Asp
            355                 360                 365
Gly Pro Tyr Gly Thr Pro Thr Arg Arg Ile Phe Ala Ser Glu His Ala
    370                 375                 380
Val Leu Ile Gly Ala Gly Ile Gly Ile Thr Pro Phe Ala Ser Ile Leu
385                 390                 395                 400
Gln Ser Ile Met Tyr Arg His Gln Lys Arg Lys His Thr Cys Pro Ser
                405                 410                 415
Cys Gln His Ser Trp Ile Glu Gly Val Gln Asp Asn Met Lys Leu His
                420                 425                 430
Lys Val Asp Phe Ile Trp Ile Asn Arg Asp Gln Arg Ser Phe Glu Trp
```

-continued

```
                435                 440                 445
Phe Val Ser Leu Leu Thr Lys Leu Glu Met Asp Gln Ala Glu Glu Ala
    450                 455                 460

Gln Tyr Gly Arg Phe Leu Glu Leu His Met Tyr Met Thr Ser Ala Leu
465                 470                 475                 480

Gly Lys Asn Asp Met Lys Ala Ile Gly Leu Gln Met Ala Leu Asp Leu
                485                 490                 495

Leu Ala Asn Lys Glu Lys Lys Asp Ser Ile Thr Gly Leu Gln Thr Arg
            500                 505                 510

Thr Gln Pro Gly Arg Pro Asp Trp Ser Lys Val Phe Gln Lys Val Ala
        515                 520                 525

Ala Glu Lys Lys Gly Lys Val Gln Val Phe Phe Cys Gly Ser Pro Ala
    530                 535                 540

Leu Ala Lys Val Leu Lys Gly His Cys Glu Lys Phe Gly Phe Arg Phe
545                 550                 555                 560

Phe Gln Glu Asn Phe
                565

<210> SEQ ID NO 5
<211> LENGTH: 3999
<212> TYPE: DNA
<213> ORGANISM: Homo sapiens

<400> SEQUENCE: 5
tgccaatttc acctggcatt atgatactaa attgcaggtg tgttcagcag ctaatgaaaa       60
tgttgttttt atgggttttg tgatgttgaa gagatttttc agcttttac aataaatata      120 aaatgtgctg tgcattgcgc tatactcctt ataatgggaa catttcatgg catataaatt      180
atacctcaat aaatctgtta attgtgctgt gctttctttt ctgttttaaa taaatatttg      240
cttttgtgcc taaagtaaag taaaataaaa atatgtagca gtatatctac aaaacctata      300
caaaacattc tacttaaggg tgaaatggaa gaatcccctt tgagattggg aattaggcaa      360
ggggatcact acttctacct tgtgcagca ttgtactaga agttctagtg agtgcagtaa       420
gcgaagaaaa agaaataaaa gttataagaa ttagaaaaaa gaaggctggg cacggtggct      480
cacgcctgta atcccagcat tttgggaggc cgaggcaggc gtatcacctg aggtcaggtg      540
tttcagacct acctggccaa catggtaaaa cccagtctct actaaaaata gaaaaattag      600
ccgagcatgg tggtgggcgc ctgtagtccc agctactcgg gaggctgagg caggagaatc      660
gcttgaaccc gggaggcaga cgttgcagta agccattgca ctccagcctg gcaacaaga      720 gggaaactcc gtctcaaaaa aaaaaaaaag aattagaaaa aagaaataaa actgtgttta      780
gagcgaaaaa tgtgactgtg tttatagaca atgtaagaca aaatcagaa atattattac       840 aattaataag tgagtttagc aatgttgctg ggcataaaaa tcaatatgta aaaacaaatt      900
gtatctttaa cagccatcat taaaaattaa aattaaaata tataatttac aacctcatga      960
aaacatataa agttcttaga agtggatata acaggctggg cacggtggct catgcctgta     1020
atcccagcac tttgggaggc cgaggcaggc ggatcacgag gtgaggaggt cgagaccatc     1080
ctggctagca cagtgaaacc ccgtctctac taaaaatag aaaaaattag ccaggcgtgg      1140
tggcgggcgc ctgtggtccc agctactcgg gaggctgagg caggagaatg gcgtgaaccc     1200
gggaggtgga gcttgcagtg agccgagatt gcaccactgc actccagcct gggcgacaga     1260
gcgagactcc gtctcaaaga aaaaaaaaaa agaagaagaa gtgaatataa caaaggagac     1320
gcaagaattt gattataaaa tttacatgaa aatgaaaaag gccaagaata aaaacaaaac     1380
```

```
acagaacccc ccctccccccc aaaacaaaga aacaaacaaa caaaaagtca agaatagcca   1440
aagcactctt gaagaacaag gtggggaaac ttgtcttatc agatgtcaag acttagtaat   1500
taaggcagtg gcatggaaga actgaatgga gagctccgga agaaactcgt gtatatagac   1560
atttcatata taatagaact gacattttag atcagcgaag aaagtatatt tttgaaagta   1620
cttttcaaaa atggctgagc gcagtggctc atgcctgtaa tcccagcact ttgagaggcc   1680
cacgtgggtg gatcacatga ggccaggagg tcaagaccag actggccagc acagcaaaac   1740
cctgtctcta ctaaaaatac aaaaattagc caggcatgat ggcgcttgcc tgtaatccca   1800
gctactcggg tggctaaggc atgagaatca cttgaaccca ggaggtgaag gttgcagtga   1860
agggagatca caccactgta ctccaacctg ggtgacagag tgagaccctg tctcaaaaaa   1920
ataaaaataa aaataaaaag tacttttcaa aaatgatgct ggggcaattc gttttccata   1980
tttaaaagta gtaaattgga taccatacat gaaaatcagc tccaggtgga ttcaaaacat   2040
aaatgtaaaa tgcaaaaata taaaatttct agaagaaaat ataaagagt atcttgatat    2100
ctgggtagtg atggatttct aaaacaagac ataaaatgca taaatcataa aagaaatgac   2160
tggtaatcag agtgcattaa aattaagaac ttccattttat cagaaaacac tattaagaga  2220
ctgaaaagac aagccataaa cataagcaat aaaagattag tataagatta taaacagaac   2280
cctaagaatc taaaagcaaa agaaaaacca atagaaagat agaccaaaaa gtagaatagg   2340
ctcagaatag gctcttttaa aaagagaaaa ctcaaatggc cagcagttga attaaaagat   2400
gctcaaactc attagtaatc agggaaatgc aaattaaaat cataatacga tagttttcca   2460
cacttacttg aattataaaa acaaaaaagt ctggaaaata ccaggggttg gtaagcatgt   2520
agaggaagta gaactctcat tcataactct ctgtagtata catttaggtg gtcacttcgg   2580
aacgggtttg gaattacaca gcaaagtaga atatgtgcaa atctcaggac cctggaattt   2640
tactcctggg tatataccctt agagaaactg tagcatatgt gtgacatttg atcaacattg  2700
ttccatcatc atatccatca gtagtaggat gaatgaatac attaatgtat attcattatg   2760
caatggcata ttagatagca gtgtaagtga accgcaatta catgtacatg tatgaatctc   2820
aaaaacccaa tgttgaaaga agcaaaccac agaagcatac atacacactg ccaggtttca   2880
tttacaaaaa gttcaaaaac aggaaaaact aaacaatata ttgcttaggg atgcaattat   2940
agttagtaaa aatataaaga aaaataacag aatgattacc ccaaatttca ggatagtgat   3000
tacatccggt ggggtagagg aggggaagaa gatagatgtg atcagggagg gaaatacaaa   3060
gagctttaag atactggaga aaaatagtct attttctttta atctgagtag tgaacacata  3120
gatacttatt ccttaaaatt attctttaag ttacatatgt atgttttata tactcttctg   3180
tgtatatttc accattttag aaaagggaaa aaaaatcagt gcccagagct gaacacacaa   3240
ctctagtaaa tctatcatac tagaagacaa tcatctccat tcttttgagt gctctgcctc   3300
tgtttatttt gaaccaaagt gcactttat acttgttaaa ttttctcttg ctctatttgg    3360
cccttctttt cacttgtcct tccagccagt caagttctcc ccaaagccat catcatatat   3420
gtcaaccaca gatcatcctc caggggaact ggtatgctaa agtttctgag ctagccaggc   3480
tgaaatccaa atggcagccg gcagatgtgg caacagtttg aaaagtgcac tttgaaacag   3540
cttccttacc acacacgctt ccctccctac ttctcctgaa gtaatctgtt tacagaccca   3600
gactaataat cttttttatg agaaacttta gcaaatcttt tatctaggaa ggcaatgctt   3660
cacattaggt catgttgata agatgatgag agagaatatt ttcatccaag aatgttgcta   3720
```

-continued

```
tttcctgaag cagtaaaatc cccacaggta aaacccttgt ggttctcata gatagggctg    3780
gtctatctaa gctgatagca cagttctgtc cagagaagga aggcagaata aacttattca    3840
ttcccaggaa ctcttggggt aggtgtgtgt ttttcacatc ttaaaggctc acagaccctg    3900
cgctggacaa atgttccatt cctgaaggac ctctccagaa tccggattgc tgaatcttcc    3960
ctgttgccta aagggctcc aaaccacctc ttgacaatg                            3999
```

<210> SEQ ID NO 6
<211> LENGTH: 2044
<212> TYPE: DNA
<213> ORGANISM: Homo sapiens

<400> SEQUENCE: 6

```
caaagacaaa ataatttact agggaagccc ttactaacga cccaacatcc agacacaggt      60
gagggagaag aaatttcctg acagccgaag agcaacaagt atcatgatgg ggtgctggat     120
tttgaatgag ggtctctcca ccatattagt actctcatgg ctgggaataa attttttatct   180 gtttattgac acgttctact ggtatgaaga ggaggagtct ttccattaca cacgagttat     240
tttgggttca acactggctt gggcacgagc atccgcactg tgcctgaatt ttaactgcat     300
gctaattcta atacctgtca gtcgaaacct tatttcattc ataagaggaa caagtatttg     360
ctgcagagga ccgtgtgagga ggcaattaga caaaaacctc agatttcaca aactggtcgc    420
ctatgggata gctgttaatg caaccatcca catcgtggcg catttcttca acctggaacg     480
ctaccactgg agccagtccg aggaggccca gggacttctg gccgcacttt ccaagctggg    540 caacaccct aacgagagct acctcaaccc tgtccggacc ttccccacaa acacaaccac      600
tgaattgcta aggacaatag caggcgtcac cggtctggtg atctctctgg ctttagtctt     660
gatcatgacc tcgtcaactg agttcatcag acaggcctcc tatgagttgt tctggtacac    720
acaccatgtt ttcatcgtct ctttctcag cctggccatc catgggacgg tcggattgt      780 tcgaggccaa acccaagaca gtctctctct gcacaacatc accttctgta gagaccgcta    840
tgcagaatgg cagacagtgg cccaatgccc cgtgcctcaa ttttctggca aggaaccctc    900
ggcttggaaa tggattttag gccctgtggt cttgtatgca tgtgaaagaa taattaggtt     960
ctggcgattt caacaagaag ttgtcattac caaggtggta agccaccct ctggagtcct    1020 ggaacttcac atgaaaaagc gtggctttaa aatggcgcca gggcagtaca tcttggtgca   1080
gtgcccagcc atatcttcgc tggagtggca cccttcacc cttacctctg cccccagga    1140 agactttttc agcgtgcaca tccgggcagc aggagactgg acagcagcgc tactggaggc    1200
ctttggggca gagggacagg ccctccagga gccctggagc ctgccaaggc tggcagtgga    1260
cgggcccttt ggaactgccc tgacagatgt atttcactac ccagtgtgtg tgtgcgttgc    1320
cgcggggatc ggagtcactc ccttcgctgc tcttctgaaa tctatatggt acaaatgcag    1380
tgaggcacag accccactga agctgagcaa ggtgtatttc tactggattt gcgggatgc     1440 aagagctttt gagtggtttg ctgatctctt actctccctg gaaacacgga tgagtgagca    1500
ggggaaaact cactttctga gttatcatat atttcttacc ggctgggatg aaaatcaggc    1560
tcttcacata gctttacact gggacgaaaa tactgacgtg attacaggct taaagcagaa    1620
gaccttctat ggggagccca actggaacaa tgagttcaag cagattgcct acaatcaccc    1680
cagcagcagt attggcgtgt cttctgtgg acctaaagct ctctcgagga cacttcaaaa     1740
gatgtgccac ttgtattcat cagctgaccc cagaggtgtt catttctatt acaacaagga    1800
gagcttctag actttggagg tcaagtccag gcattgtgtt ttcaatcaag ttattgattc    1860
```

| | | | | |
|---|---|---|---|---|
| caaagaactc | caccaggaat | tcctgtgacg | gcctgttgat | atgagctccc | agttgggaac | 1920 |
| tggtgaataa | taattaacta | ttgtgaacag | tacactatac | catacttcct | tagcttataa | 1980 |
| ataacatgtc | atatacaaca | gaacaaaaac | atttactgaa | attaaaatat | attatgtttc | 2040 |
| tcca | | | | | | 2044 |

<210> SEQ ID NO 7
<211> LENGTH: 25
<212> TYPE: DNA
<213> ORGANISM: Artificial Sequence
<220> FEATURE:
<223> OTHER INFORMATION: Synthetic Primer

<400> SEQUENCE: 7
caacgaaggg gttaaacacc tctgc        25

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
cacagctgat tgattccgct gag          23

<210> SEQ ID NO 9
<211> LENGTH: 24
<212> TYPE: DNA
<213> ORGANISM: Artificial Sequence
<220> FEATURE:
<223> OTHER INFORMATION: Synthetic Primer

<400> SEQUENCE: 9
taagccaaga gtgttcggca catg          24

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
tactctggcc cttggttata cagca         25

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
tccatttacc ctcacaatgt gt            22

<210> SEQ ID NO 12
<211> LENGTH: 23
<212> TYPE: DNA
<213> ORGANISM: Artificial Sequence
<220> FEATURE:
<223> OTHER INFORMATION: Synthetic Primer

<400> SEQUENCE: 12
ctcagcggaa tcaatcagct gtg                                          23

<210> SEQ ID NO 13
<211> LENGTH: 569
<212> TYPE: PRT
<213> ORGANISM: Homo sapiens

<400> SEQUENCE: 13

| | | | | | | | | | | | | | | |
|---|---|---|---|---|---|---|---|---|---|---|---|---|---|---|
| Gly | Asn | Trp | Ala | Val | Asn | Glu | Gly | Leu | Ser | Ile | Phe | Ala | Ile | Leu | Val |
| 1 | | | | 5 | | | | | 10 | | | | | 15 | |
| Trp | Leu | Gly | Leu | Asn | Val | Phe | Leu | Phe | Val | Trp | Tyr | Tyr | Arg | Val | Tyr |
| | | | 20 | | | | | 25 | | | | | 30 | | |
| Asp | Ile | Pro | Pro | Lys | Phe | Phe | Tyr | Thr | Arg | Lys | Leu | Leu | Gly | Ser | Ala |
| | | | 35 | | | | | 40 | | | | | 45 | | |
| Leu | Ala | Leu | Ala | Arg | Ala | Pro | Ala | Ala | Cys | Leu | Asn | Phe | Asn | Cys | Met |
| | 50 | | | | | 55 | | | | | 60 | | | | |
| Leu | Ile | Leu | Leu | Pro | Val | Cys | Arg | Asn | Leu | Leu | Ser | Phe | Leu | Arg | Gly |
| 65 | | | | | 70 | | | | | 75 | | | | | 80 |
| Ser | Ser | Ala | Cys | Cys | Ser | Thr | Arg | Val | Arg | Arg | Gln | Leu | Asp | Arg | Asn |
| | | | | 85 | | | | | 90 | | | | | 95 | |
| Leu | Thr | Phe | His | Lys | Met | Val | Ala | Trp | Met | Ile | Ala | Leu | His | Ser | Ala |
| | | | | 100 | | | | | 105 | | | | | 110 | |
| Ile | His | Thr | Ile | Ala | His | Leu | Phe | Asn | Val | Glu | Trp | Cys | Val | Asn | Ala |
| | | | 115 | | | | | 120 | | | | | 125 | | |
| Arg | Val | Asn | Asn | Ser | Asp | Pro | Tyr | Ser | Val | Ala | Leu | Ser | Glu | Leu | Gly |
| | 130 | | | | | 135 | | | | | 140 | | | | |
| Asp | Arg | Gln | Asn | Glu | Ser | Tyr | Leu | Asn | Phe | Ala | Arg | Lys | Arg | Ile | Lys |
| 145 | | | | | 150 | | | | | 155 | | | | | 160 |
| Asn | Pro | Glu | Gly | Gly | Leu | Tyr | Leu | Ala | Val | Thr | Leu | Leu | Ala | Gly | Ile |
| | | | | 165 | | | | | 170 | | | | | 175 | |
| Thr | Gly | Val | Val | Ile | Thr | Leu | Cys | Leu | Ile | Leu | Ile | Ile | Thr | Ser | Ser |
| | | | 180 | | | | | 185 | | | | | 190 | | |
| Thr | Lys | Thr | Ile | Arg | Arg | Ser | Tyr | Phe | Glu | Val | Phe | Trp | Tyr | Thr | His |
| | | 195 | | | | | 200 | | | | | 205 | | | |
| His | Leu | Phe | Val | Ile | Phe | Phe | Ile | Gly | Leu | Ala | Ile | His | Gly | Ala | Glu |
| | 210 | | | | | 215 | | | | | 220 | | | | |
| Arg | Ile | Val | Arg | Gly | Gln | Thr | Ala | Glu | Ser | Leu | Ala | Val | His | Asn | Ile |
| 225 | | | | | 230 | | | | | 235 | | | | | 240 |
| Thr | Val | Cys | Glu | Gln | Lys | Ile | Ser | Glu | Trp | Gly | Lys | Ile | Lys | Glu | Cys |
| | | | | 245 | | | | | 250 | | | | | 255 | |
| Pro | Ile | Pro | Gln | Phe | Ala | Gly | Asn | Pro | Pro | Met | Thr | Trp | Lys | Trp | Ile |
| | | | 260 | | | | | 265 | | | | | 270 | | |
| Val | Gly | Pro | Met | Phe | Leu | Tyr | Leu | Cys | Glu | Arg | Leu | Val | Arg | Phe | Trp |
| | | 275 | | | | | 280 | | | | | 285 | | | |
| Arg | Ser | Gln | Gln | Lys | Val | Val | Ile | Thr | Lys | Val | Val | Thr | His | Pro | Phe |
| | | 290 | | | | | 295 | | | | | 300 | | | |
| Lys | Thr | Ile | Glu | Leu | Gln | Met | Lys | Lys | Lys | Gly | Phe | Lys | Met | Glu | Val |
| 305 | | | | | 310 | | | | | 315 | | | | | 320 |
| Gly | Gln | Tyr | Ile | Phe | Val | Lys | Cys | Pro | Lys | Val | Ser | Lys | Leu | Glu | Trp |
| | | | | 325 | | | | | 330 | | | | | 335 | |
| His | Pro | Phe | Thr | Leu | Thr | Ser | Ala | Pro | Glu | Glu | Asp | Phe | Phe | Ser | Ile |
| | | | 340 | | | | | 345 | | | | | 350 | | |
| His | Ile | Arg | Ile | Val | Gly | Asp | Trp | Thr | Glu | Gly | Leu | Phe | Asn | Ala | Cys |
| | | 355 | | | | | 360 | | | | | 365 | | | |

-continued

```
Gly Cys Asp Lys Gln Glu Phe Gln Asp Ala Trp Lys Leu Pro Lys Ile
            370                 375                 380

Ala Val Asp Gly Pro Phe Gly Thr Ala Ser Glu Asp Val Phe Ser Tyr
385                 390                 395                 400

Glu Val Val Met Leu Val Gly Ala Gly Ile Gly Val Thr Pro Phe Ala
                405                 410                 415

Ser Ile Leu Lys Ser Val Trp Tyr Lys Tyr Cys Asn Asn Ala Thr Asn
            420                 425                 430

Leu Lys Leu Lys Lys Ile Tyr Phe Tyr Trp Leu Cys Arg Asp Thr His
        435                 440                 445

Ala Phe Glu Trp Phe Ala Asp Leu Leu Gln Leu Leu Glu Ser Gln Met
450                 455                 460

Gln Glu Arg Asn Asn Ala Gly Phe Leu Ser Tyr Asn Ile Tyr Leu Thr
465                 470                 475                 480

Gly Trp Asp Glu Ser Gln Ala Asn His Phe Ala Val His His Asp Glu
                485                 490                 495

Glu Lys Asp Val Ile Thr Gly Leu Lys Gln Lys Thr Leu Tyr Gly Arg
            500                 505                 510

Pro Asn Trp Asp Asn Glu Phe Lys Thr Ile Ala Ser Gln His Pro Asn
        515                 520                 525

Thr Arg Ile Gly Val Phe Leu Cys Gly Pro Glu Ala Leu Ala Glu Thr
530                 535                 540

Leu Ser Lys Gln Ser Ile Ser Asn Ser Glu Ser Gly Pro Arg Gly Val
545                 550                 555                 560

His Phe Ile Phe Asn Lys Glu Asn Phe
                565

<210> SEQ ID NO 14
<211> LENGTH: 564
<212> TYPE: PRT
<213> ORGANISM: Homo sapiens

<400> SEQUENCE: 14

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
            20                  25                  30

Tyr Glu Lys Ala Asp Lys Tyr Tyr Tyr Thr Arg Lys Ile Leu Gly Ser
        35                  40                  45

Thr Leu Ala Cys Ala Arg Ala Ser Ala Leu Cys Leu Asn Phe Asn Ser
    50                  55                  60

Thr Leu Ile Leu Leu Pro Val Cys Arg Asn Leu Leu Ser Phe Leu Arg
65                  70                  75                  80

Gly Thr Cys Ser Phe Cys Ser Arg Thr Leu Arg Lys Gln Leu Asp His
                85                  90                  95

Asn Leu Thr Phe His Lys Leu Val Ala Tyr Met Ile Cys Leu His Thr
            100                 105                 110

Ala Ile His Ile Ile Ala His Leu Phe Asn Phe Asp Cys Tyr Ser Arg
        115                 120                 125

Ser Arg Gln Ala Thr Asp Gly Ser Leu Ala Ser Ile Leu Ser Ser Leu
    130                 135                 140

Ser His Asp Glu Lys Lys Gly Gly Ser Trp Leu Asn Pro Ile Gln Ser
145                 150                 155                 160

Arg Asn Thr Thr Val Glu Tyr Val Thr Phe Thr Ser Val Ala Gly Leu
                165                 170                 175
```

```
Thr Gly Val Ile Met Thr Ile Ala Leu Ile Leu Met Val Thr Ser Ala
            180                 185                 190
Thr Glu Phe Ile Arg Arg Ser Tyr Phe Glu Val Phe Trp Tyr Thr His
            195                 200                 205
His Leu Phe Ile Phe Tyr Ile Leu Gly Leu Gly Ile His Gly Ile Gly
            210                 215                 220
Gly Ile Val Arg Gly Gln Thr Glu Glu Ser Met Asn Glu Ser His Pro
225                 230                 235                 240
Arg Lys Cys Ala Glu Ser Phe Glu Met Trp Asp Asp Arg Asp Ser His
                    245                 250                 255
Cys Arg Arg Pro Lys Phe Glu Gly His Pro Pro Glu Ser Trp Lys Trp
                    260                 265                 270
Ile Leu Ala Pro Val Ile Leu Tyr Ile Cys Glu Arg Ile Leu Arg Phe
                    275                 280                 285
Tyr Arg Ser Gln Gln Lys Val Val Ile Thr Lys Val Val Met His Pro
            290                 295                 300
Ser Lys Val Leu Glu Leu Gln Met Asn Lys Arg Gly Phe Ser Met Glu
305                 310                 315                 320
Val Gly Gln Tyr Ile Phe Val Asn Cys Pro Ser Ile Ser Leu Leu Glu
                    325                 330                 335
Trp His Pro Phe Thr Leu Thr Ser Ala Pro Glu Glu Asp Phe Phe Ser
                    340                 345                 350
Ile His Ile Arg Ala Ala Gly Asp Trp Thr Glu Asn Leu Ile Arg Ala
                    355                 360                 365
Phe Glu Gln Gln Tyr Ser Pro Ile Pro Arg Ile Glu Val Asp Gly Pro
            370                 375                 380
Phe Gly Thr Ala Ser Glu Asp Val Phe Gln Tyr Glu Val Ala Val Leu
385                 390                 395                 400
Val Gly Ala Gly Ile Gly Val Thr Pro Phe Ala Ser Ile Leu Lys Ser
                    405                 410                 415
Ile Trp Tyr Lys Phe Gln Cys Ala Asp His Asn Leu Lys Thr Lys Lys
                    420                 425                 430
Ile Tyr Phe Tyr Trp Ile Cys Arg Glu Thr Gly Ala Phe Ser Trp Phe
            435                 440                 445
Asn Asn Leu Leu Thr Ser Leu Glu Gln Glu Met Glu Glu Leu Gly Lys
            450                 455                 460
Val Gly Phe Leu Asn Tyr Arg Leu Phe Leu Thr Gly Trp Asp Ser Asn
465                 470                 475                 480
Ile Val Gly His Ala Ala Leu Asn Phe Asp Lys Ala Thr Asp Ile Val
                    485                 490                 495
Thr Gly Leu Lys Gln Lys Thr Ser Phe Gly Arg Pro Met Trp Asp Asn
                    500                 505                 510
Glu Phe Ser Thr Ile Ala Thr Ser His Pro Lys Ser Val Val Gly Val
            515                 520                 525
Phe Leu Cys Gly Pro Arg Thr Leu Ala Lys Ser Leu Arg Lys Cys Cys
            530                 535                 540
His Arg Tyr Ser Ser Leu Asp Pro Arg Lys Val Gln Phe Tyr Phe Asn
545                 550                 555                 560
Lys Glu Asn Phe

<210> SEQ ID NO 15
<211> LENGTH: 24
<212> TYPE: DNA
```

```
<213> ORGANISM: Artificial Sequence
<220> FEATURE:
<223> OTHER INFORMATION: Synthetic Primer

<400> SEQUENCE: 15
ctcattgtca cactcctcga cagc                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic Primer

<400> SEQUENCE: 16
tgggtctgat gccttgaagg actc                                              24

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
atcaagcggc cccctttttt tcac                                              24

<210> SEQ ID NO 18
<211> LENGTH: 24
<212> TYPE: DNA
<213> ORGANISM: Artificial Sequence
<220> FEATURE:
<223> OTHER INFORMATION: Synthetic Primer

<400> SEQUENCE: 18
ctgaacatcc ccaccattgc tcgc                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic Primer

<400> SEQUENCE: 19
ctgaacatcc ccaccattgc tcgc                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic Primer

<400> SEQUENCE: 20
gaagccgaac ttctcacaat ggcc                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic Primer

<400> SEQUENCE: 21
cctcacctct ccaagctctg cccc                                              24
```

<210> SEQ ID NO 22
<211> LENGTH: 24
<212> TYPE: DNA
<213> ORGANISM: Artificial Sequence
<220> FEATURE:
<223> OTHER INFORMATION: Synthetic Primer

<400> SEQUENCE: 22
ttgaacaatt ttataagatg ccgg                                          24

<210> SEQ ID NO 23
<211> LENGTH: 25
<212> TYPE: DNA
<213> ORGANISM: Artificial Sequence
<220> FEATURE:
<223> OTHER INFORMATION: Synthetic Primer

<400> SEQUENCE: 23
agaggaacac gacaatcagc cttag                                         25

<210> SEQ ID NO 24
<211> LENGTH: 25
<212> TYPE: DNA
<213> ORGANISM: Artificial Sequence
<220> FEATURE:
<223> OTHER INFORMATION: Synthetic Primer

<400> SEQUENCE: 24
ggagtttcaa gatgcgtgga aacta                                         25

<210> SEQ ID NO 25
<211> LENGTH: 31
<212> TYPE: DNA
<213> ORGANISM: Artificial Sequence
<220> FEATURE:
<223> OTHER INFORMATION: Synthetic Primer

<400> SEQUENCE: 25
gctactcgag tgtgccaatt tcacctggca t                                  31

<210> SEQ ID NO 26
<211> LENGTH: 31
<212> TYPE: DNA
<213> ORGANISM: Artificial Sequence
<220> FEATURE:
<223> OTHER INFORMATION: Synthetic Primer

<400> SEQUENCE: 26
aactctcgag tgtcaagagg tggtttggag c                                  31

<210> SEQ ID NO 27
<211> LENGTH: 789
<212> TYPE: DNA
<213> ORGANISM: Homo sapiens
<220> FEATURE:
<221> NAME/KEY: misc_feature
<222> LOCATION: (581)..(581)
<223> OTHER INFORMATION: "n "= any nucleotide
<220> FEATURE:
<221> NAME/KEY: misc_feature
<222> LOCATION: (587)..(587)
<223> OTHER INFORMATION: "n "= any nucleotide
<220> FEATURE:
<221> NAME/KEY: misc_feature
<222> LOCATION: (620)..(620)
<223> OTHER INFORMATION: "n "= any nucleotide

```
<400> SEQUENCE: 27
agcttcaatt attttttaat tttgttcaat cttgcatttg ttcaaccaaa aacaatttaa      60
agaggaacac gacaatcagc cttagattga gcaagttcag ctcctcacta gggagttctt     120
gaatccacca tgaaaatcaa cagtgtgcat ctaacagttt tctttaatt tgagaactga      180 aaagtgaatc atcacatcaa atattcttca gggtctcttt ggtttccaga ttaaacatgt     240
aatgtgacgg tcatcttgcc acattctcac atttccattt taaataatca taaataagaa     300
aaccttacta ttctttggca taacacagct gattgattcc gctgagtttc aaagtcttag     360
aaattgcact cattccttct ttagagtcct gcttcatggc aaaagttttc agctgaaaga     420
ctctttattg tattcaaatc ttgtcccata tgagttgttc tggttactca gtttatgaag     480
agtcttggat agtgaattgg gtccacaaca gaaaacacca actgttttc ctctgttata     540 ttttgctatt tcatcaaaca aaagtttcca ccggagacgt nctatanaca gtcttgaatt     600
cagtgcatga tattttctn caattatctt ctgtatccca tctgtttgac tgacgtacag     660
cctgatgttg acatagtcag gtctggtctc ttgccaaaac ttgtatgcaa catacagagt     720
aaatctggca accaacggaa ggactggata tctctgccta ccccaaataa agtatgtctt     780
tcttagctt                                                            789

<210> SEQ ID NO 28
<211> LENGTH: 408
<212> TYPE: DNA
<213> ORGANISM: Homo sapiens

<400> SEQUENCE: 28 ttttttttttt tattagaaga aacctttct tgtttattga attataatta tttatttgtt     60 ggttttttcca ttatattgta agcaacttga ggggcgaggt gaggtcttac tctctgggtg    120
cccatctgaa atgtataggt ttcaagacag ttcccccaac atctggtgga ggtagtgata    180
ctctggccct tggttataca gcaagaaggt tttccagaaa agcaggacat tcatggagag    240
ccagatgaac aggcagaggt gtttaacccc ttcgttggcg agccagctcc tccaggacac    300
aggcatgccg ccggccccgc cgcgctgcgc tctgtgcccg ccggcccgag aaggagcggg    360
cggcggccgg ggcagcggtt acagttgtgc ggcctgccgg ccgctga                 408

<210> SEQ ID NO 29
<211> LENGTH: 2044
<212> TYPE: DNA
<213> ORGANISM: Homo sapiens

<400> SEQUENCE: 29
caaagacaaa ataatttact agggaagccc ttactaacga cccaacatcc agacacaggt    60
gagggagaag aaatttcctg acagccgaag agcaacaagt atcatgatgg ggtgctggat    120
tttgaatgag ggtctctcca ccatattagt actctcatgg ctgggaataa attttttatct   180 gtttattgac acgttctact ggtatgaaga ggaggagtct ttccattaca cacgagttat    240
tttgggttca acactggctt gggcacgagc atccgcactg tgcctgaatt ttaactgcat    300
gctaattcta ataccgtgca gtcgaaacct tatttcattc ataagaggaa caagtatttg    360
ctgcagagga ccgtggagga ggcaattaga caaaaacctc agatttcaca aactggtcgc    420 ctatggggata gctgttaatg caaccatcca catcgtggcg catttcttca acctggaacg    480
ctaccactgg agccagtccg aggaggccca gggacttctg gccgcacttt ccaagctggg    540
caacacccct aacgagagct acctcaaccc tgtccggacc ttccccacaa acacaaccac    600
```

```
tgaattgcta aggacaatag caggcgtcac cggtctggtg atctctctgg ctttagtctt        660
gatcatgacc tcgtcaactg agttcatcag acaggcctcc tatgagttgt tctggtacac        720
acaccatgtt ttcatcgtct tctttctcag cctggccatc catgggacgg tcggattgt         780 tcgaggccaa acccaagaca gtctctctct gcacaacatc accttctgta gagaccgcta        840
tgcagaatgg cagacagtgg cccaatgccc cgtgcctcaa ttttctggca aggaaccctc        900
ggcttggaaa tggattttag gccctgtggt cttgtatgca tgtgaaagaa taattaggtt        960
ctggcgattt caacaagaag ttgtcattac caaggtggta agccacccct ctggagtcct       1020
ggaacttcac atgaaaaagc gtggctttaa atggcgcca gggcagtaca tcttggtgca        1080
gtgcccagcc atatcttcgc tggagtggca ccccttcacc cttacctctg ccccccagga       1140 agacttttc agcgtgcaca tccgggcagc aggagactgg acagcagcgc tactggaggc        1200
ctttggggca gagggacagg ccctccagga gccctggagc ctgccaaggc tggcagtgga       1260
cgggcccttt ggaactgccc tgacagatgt atttcactac ccagtgtgtg tgtgcgttgc       1320 cgcgggatc ggagtcactc ccttcgctgc tcttctgaaa tctatatggt acaaatgcag        1380
tgaggcacag accccactga agctgagcaa ggtgtatttc tactggattt gccgggatgc       1440
aagagctttt gagtggtttg ctgatctctt actctccctg gaaacacgga tgagtgagca       1500
ggggaaaact cactttctga gttatcatat atttcttacc ggctgggatg aaaatcaggc       1560
tcttcacata gctttacact gggacgaaaa tactgacgtg attacaggct aaagcagaa        1620 gaccttctat gggaggccca actggaacaa tgagttcaag cagattgcct acaatcaccc       1680
cagcagcagt attggcgtgt tcttctgtgg acctaaagct ctctcgagga cacttcaaaa       1740
gatgtgccac ttgtattcat cagctgaccc cagaggtgtt catttctatt acaacaagga       1800
gagcttctag actttggagg tcaagtccag gcattgtgtt ttcaatcaag ttattgattc       1860
caaagaactc caccaggaat tcctgtgacg gcctgttgat atgagctccc agttgggaac       1920
tggtgaataa taattaacta ttgtgaacag tacactatac catacttcct tagcttataa       1980
ataacatgtc atatacaaca gaacaaaaac atttactgaa attaaaatat attatgtttc       2040
tcca                                                                    2044
```

<210> SEQ ID NO 30
<211> LENGTH: 2232
<212> TYPE: DNA
<213> ORGANISM: Homo sapiens

<400> SEQUENCE: 30

```
ccgcacaact gtaaccgctg ccccggccgc cgcccgctcc ttctcgggcc ggcgggcaca         60
gagcgcagcg cggcggggcc ggcggcatgg ctgtgtcctg gaggagctgg ctcgccaacg        120
aaggggttaa acacctctgc ctgttcatct ggctctccat gaatgtcctg cttttctgga       180
aaaccttctt gctgtataac caagggccag agtatcacta cctccaccag atgttggggc       240
taggattgtg tctaagcaga gcctcagcat ctgttcttaa cctcaactgc agccttatcc       300
ttttacccat gtgccgaaca ctcttggctt acctccgagg atcacagaag gttccaagca       360
ggagaaccag gagattgttg gataaaagca gaacattcca tattacctgt ggtgttacta       420
tctgtatttt ctcaggcgtg catgtggctg cccatctggt gaatgccctc aacttctcag       480
tgaattacag tgaagacttt gttgaactga atgcagcaag ataccgagat gaggatccta       540
gaaaacttct cttcacaact gttcctggcc tgacaggggt ctgcatggtg gtggtgctat       600
```

| | |
|---|---|
| tcctcatgat cacagcctct acatatgcaa taagagtttc taactatgat atcttctggt | 660 |
| atactcataa cctcttcttt gtcttctaca tgctgctgac gttgcatgtt tcaggagggc | 720 |
| tgctgaagta tcaaactaat ttagataccc accctcccgg ctgcatcagt cttaaccgaa | 780 |
| ccagctctca gaatatttcc ttaccagagt atttctcaga acattttcat gaacctttcc | 840 |
| ctgaaggatt ttcaaaaccg gcagagttta cccagcacaa atttgtgaag atttgtatgg | 900 |
| aagagcccag attccaagct aattttccac agacttggct ttggatttct ggacctttgt | 960 |
| gcctgtactg tgccgaaaga ctttacaggt atatccggag caataagcca gtcaccatca | 1020 |
| tttcggtcat aagtcatccc tcagatgtca tggaaatccg aatggtcaaa gaaattttta | 1080 |
| aagcaagacc tggtcagtat attactctac attgtcccag tgtatctgca ttagaaaatc | 1140 |
| atccatttac cctcacaatg tgtccaactg aaaccaaagc aacatttggg gttcatctta | 1200 |
| aaatagtagg agactggaca gaacgatttc gagatttact actgcctcca tctagtcaag | 1260 |
| actccgaaat tctgcccttc attcaatcta gaaattatcc caagctgtat attgatggtc | 1320 |
| cttttggaag tccatttgag gaatcactga actatgaggt cagcctctgc gtggctggag | 1380 |
| gcattggagt aactccattt gcatcaatac tcaacaccct gttggatgac tggaaaccat | 1440 |
| acaagcttag aagactatac tttatttggg tatgcagaga tatccagtcc ttccgttggt | 1500 |
| ttgcagattt actctgtatg ttgcataaca agttttggca agagaacaga cctgactatg | 1560 |
| tcaacatcca gctgtacctc agtcaaacag atgggataca aagataatt ggagaaaaat | 1620 |
| atcatgcact gaattcaaga ctgtttatag gacgtcctcg gtggaaactt ttgtttgatg | 1680 |
| aaatagcaaa atataacaga ggaaaaacag ttggtgtttt ctgttgtgga cccaattcac | 1740 |
| tatccaagac tcttcataaa ctgagtaacc agaacaactc atatgggaca agatttgaat | 1800 |
| acaataaaga gtctttcagc tgaaaacttt tgccatgaag caggactcta agaaggaat | 1860 |
| gagtgcaatt tctaagactt tgaaactcag cggaatcaat cagctgtgtt atgccaaaga | 1920 |
| atagtaaggt tttcttattt atgattattt gaaaatggaa atgtgagaat gtggcaacat | 1980 |
| gaccgtcaca ttcatgtttt aatctggaaa ccaaagagac cctgaagaat atttgatgtg | 2040 |
| atgattcatt ttcagttctc aaattaaaag aaaactgtta gatgcacact gttgattttc | 2100 |
| atggtggatt caagaactcc ctagtgagga gctgaacttg ctcaatctaa ggctgattgt | 2160 |
| cgtgttcctc tttaaattgt ttttggttga acaaatgcaa gattgaacaa aattaaaaat | 2220 |
| tcattgaagc tg | 2232 |

<210> SEQ ID NO 31
<211> LENGTH: 2199
<212> TYPE: DNA
<213> ORGANISM: Homo sapiens

<400> SEQUENCE: 31

| | |
|---|---|
| gccgacgcgg acggcaacgg ggccatcacc ttcgaggagc tccgggacga gctgcagcgc | 60 |
| ttccccggag tcatggagaa cctgaccatc agcactgccc actggctgac ggccccgcc | 120 |
| ccccgcccac gcccgcgccg gccgcgccag ctgacccgcg cctactggca caaccaccgc | 180 |
| agccagctgt tctgcctggc cacctatgca ggcctccacg tgctgctctt cgggctggcg | 240 |
| gccagcgcgc accgggacct cggcgccagc gtcatggtgg ccaagggctg tggccagtgc | 300 |
| ctcaacttcg actgcagctt catcgcggtg ctgatgctca cgctgcct cacctggctg | 360 |
| cgggccacgt ggctggctca gtcctacca ctggaccaga acatccagtt ccaccagctt | 420 |
| atgggctacg tggtagtggg gctgtccctc gtgcacactg tggctcacac tgtgaacttt | 480 |

```
gtactccagg ctcaggcgga ggccagccct ttccagttct gggagctgct gctcaccacg    540
aggcctggca ttggctgggt acacggttcg gcctccccga caggtgtcgc tctgctgctg    600
ctgctcctcc tcatgttcat ctgctccagt tcctgcatcc gcaggagtgg ccactttgag    660
gtgttctatt ggactcacct gtcctacctc ctcgtgtggc ttctgctcat ctttcatggg    720
cccaacttct ggaagtggct gctggtgcct ggaatcttgt ttttcctgga gaaggccatc    780
ggactggcag tgtcccgcat ggcagccgtg tgcatcatgg aagtcaacct cctcccctcc    840
aaggtcactc atctcctcat caagcggccc ccttttttc actatagacc tggtgactac    900
ttgtatctga acatccccac cattgctcgc tatgagtggc accccttcac catcagcagt    960
gctcctgagc agaaagacac tatctggctg cacattcggt cccaaggcca gtggacaaac    1020
aggctgtatg agtccttcaa ggcatcagac ccactgggcc gtggttctaa gaggctgtcg    1080
aggagtgtga caatgagaaa gagtcaaagg tcgtccaagg gctctgagat acttttggag    1140
aaacacaaat tctgtaacat caagtgctac atcgatgggc cttatgggac ccccacccgc    1200
aggatctttg cctctgagca tgccgtgctc atcggggcag gcatcggcat cacccccttt    1260
gcttccattc tgcagagtat catgtacagg caccagaaaa gaaagcatac ttgccccagc    1320
tgccagcact cctggatcga aggtgtccaa gacaacatga agctccataa ggtggacttt    1380
atctggatca acagagacca gcggtctttc gagtggtttg tgagcctgct gactaaactg    1440
gagatggacc aggccgagga ggctcaatac ggccgcttcc tggagctgca tatgtacatg    1500
acatctgcac tgggcaagaa tgacatgaag gccattggcc tgcagatggc ccttgacctc    1560
ctggccaaca aggagaagaa agactccatc acggggctgc agacgcgcac ccagcctggg    1620
cggcctgact ggagcaaggt gttccagaaa gtggctgctg agaagaaggg caaggtgcag    1680
gtcttcttct gtggctcccc agctctggcc aaggtgctga agggccattg tgagaagttc    1740
ggcttcagat tttccaaga gaatttctag cctcacctct ccaagctctg ccccaagtcc    1800
acaccatggg tctgcttcat cgcattagta taaatgcccc cacagggacc agcctcagat    1860
gacccaccca ataagacaaa gcctaggac cccctaatcc tgctcaacag agagaacagg    1920
agaccccaag gggcagatga acttcctcta gaacccaggg gaaggggcag tgccttgttc    1980
agtctgctgt agattctggg gtttctgtga aagtgaggga accagaggct ggtcacggga    2040
gcttgggggt ggggttcgag ggggcagagg gcaaccactc ctccaaacat tttccgacgg    2100
agccttcccc cacatccatg gtcccaaacc tgcccaatca tcacagtcat ttggaagctt    2160
atttctccgg catcttataa aattgttcaa acctacagt                           2199
```

<210> SEQ ID NO 32
<211> LENGTH: 96
<212> TYPE: DNA
<213> ORGANISM: Homo sapiens

<400> SEQUENCE: 32

```
ttgagcctcc tcggcctggt ccatctccag tttagtcagc aggctcacaa accactcgaa    60
agaccgctgg tctctgttga tccagataaa gtccac                               96
```

<210> SEQ ID NO 33
<211> LENGTH: 120
<212> TYPE: DNA
<213> ORGANISM: Homo sapiens

<400> SEQUENCE: 33

```
cctgtacatg atactctgca gaatggaagc aaaggggtg atgccgatgc ctgccccgat      60
gagcacggca tgctcagagg caaagatcct gcgggtgggg gtcccataag gcccatcgat    120

<210> SEQ ID NO 34
<211> LENGTH: 96
<212> TYPE: DNA
<213> ORGANISM: Homo sapiens

<400> SEQUENCE: 34
ctgctcagga gcactgctga tggtgaaggg gtgccactca tagcgagcaa tggtggggat     60
gttcagatac aagtagtcac caggtctata gtgaaa                              96
```

MITOGENIC OXYGENASE REGULATORS

CROSS REFERENCE TO RELATED APPLICATIONS

This application is a divisional of U.S. patent application Ser. No. 10/850,060 filed May 20, 2004 now U.S. Pat. No. 7,202,052, which is incorporated herein by reference. U.S. patent application Ser. No. 10/850,060 is a Continuation of U.S. patent application Ser. No. 09/999,248, filed Nov. 15, 2001 now U.S. Pat. No. 6,846,672, which claims priority to U.S. Provisional Patent Application No. 60/249,305 filed Nov. 16, 2000, U.S. Provisional Patent Application No. 60/251,364 filed Dec. 5, 2000, U.S. Provisional Patent Application No. 60/289,172 filed May 7, 2001, and U.S. Provisional Patent Application No. 60/289,537, filed May 7, 2001.

The U.S. Government has a paid-up license in this invention and the right in limited circumstances to require the patent owner to license others on reasonable terms as provided for by the terms of National Institutes of Health grants HL38206, HL58000, and CA84138.

TECHNICAL FIELD

The present invention relates to the field of normal and abnormal cell growth, in particular mitogenic regulation. The present invention provides the following: nucleotide sequences encoding for the production of enzymes that are mitogenic regulators; amino acid sequences of these enzymes; vectors containing these nucleotide sequences; methods for transfecting cells with vectors that produce these enzymes; transfected cells; methods for administering these transfected cells to animals to induce tumor formation; antibodies to these enzymes that are useful for detecting and measuring levels of these enzymes, and for binding to cells possessing extracellular epitopes of these enzymes; and assays for screening for effectors of these enzymes.

BACKGROUND OF THE INVENTION

Reactive oxygen intermediates (ROI) are cytotoxic and mutagenic. ROIs modify and damage critical biomolecules including DNA and lipids. The are partial reduction products of oxygen: 1 electron reduces $O_2$ to form superoxide ($O_2^-$), and 2 electrons reduce $O_2$ to form hydrogen peroxide ($H_2O_2$). The cytotoxic property of ROI is exploited by phagocytes, which generate large amounts of superoxide and hydrogen peroxide as part of their armory of bactericidal mechanisms. ROI have been considered an accidental byproduct of metabolism, particularly mitochondrial respiration. Recent studies give evidence for regulated enzymatic generation of $O_2^-$ and its conversion to $H_2O_2$ in a variety of cells. The conversion of $O_2^-$ to $H_2O_2$ can also occur spontaneously, but is markedly accelerated by superoxide dismutase (SOD). Exposure of cells to platelet derived growth factor and epidermal growth factor induces the production of $H_2O_2$, which activates components of signaling pathways including p42/p44 MAPK and tyrosine phosphroylation.

Several biological systems generate reactive oxygen. Exposure of neutrophils to bacteria or to various soluble mediators such as formyl-Met-Leu-Phe or phorbol esters activates a massive consumption of oxygen, termed the respiratory burst, to initially generate superoxide, with secondary generation of $H_2O_2$, HOCl and hydroxyl radical. The enzyme responsible for this oxygen consumption is the respiratory burst oxidase (nicotinamide adenine dinucleotide phosphate-reduced form (NADPH) oxidase).

There is also growing evidence for the generation of ROI by non-phagocytic cells, particularly in situations related to cell proliferation. Significant generation of $H_2O_2$, $O_2^-$, or both have been noted in some cell types. Fibroblasts and human endothelial cells show increased release of superoxide in response to cytokines such as interleukin-1 or tumor necrosis factor (TNF) (Meier et al. (1989) *Biochem J.* 263, 539-545; Matsubara et al. (1986) *J. Immun.* 137, 3295-3298). Ras-transformed fibroblasts show increased superoxide release compared with control fibroblasts (Irani, et al. (1997) *Science* 275, 1649-1652). Rat vascular smooth muscle cells show increased $H_2O_2$ release in response to PDGF (Sundaresan et al. (1995) *Science* 270, 296-299) and angiotensin II (Griendling et al. (1994) *Circ. Res.* 74, 1141-1148; Fukui et al. (1997) *Circ. Res.* 80, 45-51; Ushio-Fukai et al. (1996) *J. Biol. Chem.* 271, 23317-23321), and $H_2O_2$ in these cells is associated with increased proliferation rate. $H_2O_2$ in the transformed fibroblasts and in vascular smooth muscle cells is associated with an increased proliferation rate. The occurrence of ROI in a variety of cell types is summarized in Table 1 (adapted from Burdon, R. (1995) *Free Radical Biol. Med.* 18, 775-794).

TABLE 1

| Superoxide | Hydrogen Peroxide |
| --- | --- |
| human fibroblasts | Balb/3T3 cells |
| human endothelial cells | rat pancreatic islet cells |
| human/rat smooth muscle cells | murine keratinocytes |
| human fat cells | rabbit chondrocytes |
| human osteocytes | human tumor cells |
| BHK-21 cells | fat cells, 3T3 L1 cells |
| human colonic epithelial cells | |

ROI generated by neutrophils have a cytotoxic function. While ROI are normally directed at the invading microbe, ROI can also induce tissue damage (e.g., in inflammatory conditions such as arthritis, shock, lung disease, and inflammatory bowel disease) or may be involved in tumor initiation or promotion, due to damaging effects on DNA. Nathan (Szatrowski et al. (1991) *Canc. Res.* 51, 794-798) proposed that the generation of ROI in tumor cells may contribute to the hypermutability seen in tumors, and may therefore contribute to tumor heterogeneity, invasion and metastasis.

In addition to cytotoxic and mutagenic roles, ROI have ideal properties as signal molecules: 1) they are generated in a controlled manner in response to upstream signals; 2) the signal can be terminated by rapid metabolism of $O_2^-$ and $H_2O_2$ by SOD and catalase/peroxidases; 3) they elicit downstream effects on target molecules, e.g., redox-sensitive regulatory proteins such as NFκ-B and AP-1 (Schreck et al. (1991) *EMBO J.* 10, 2247-2258; Schmidt et al. (1995) *Chemistry & Biology* 2, 13-22). Oxidants such as $O_2^-$ and $H_2O_2$ have a relatively well defined signaling role in bacteria, operating via the SoxI/II regulon to regulate transcription.

ROI appear to have a direct role in regulating cell division, and may function as mitogenic signals in pathological conditions related to growth. These conditions include cancer and cardiovascular disease. $O_2^-$ is generated in endothelial cells in response to cytokines, and might play a role in angiogenesis (Matsubara et al. (1986) *J. Immun.* 137, 3295-3298). $O_2^-$ and $H_2O_2$ are also proposed to function as "life-signals", preventing cells from undergoing apoptosis (Matsubara et al. (1986) *J. Immun.* 137, 3295-3298). As discussed above, many cells respond to growth factors (e.g., platelet derived growth factor (PDGF), epidermal derived growth factor (EGF), angiotensin II, and various cytokines) with both increased production of $O_2^-/H_2O_2$ and increased proliferation. Inhibition of ROI generation prevents the mitogenic response. Exposure to exogenously generated $O_2^-$ and $H_2O_2$ results in an increase in cell proliferation. A partial list of responsive cell types is shown below in Table 2 (adapted from Burdon, R. (1995) *Free Radical Biol. Med.* 18, 775-794).

TABLE 2

| Superoxide | Hydrogen peroxide |
| --- | --- |
| human, hamster fibroblasts | mouse osteoblastic cells |
| Balb/3T3 cells | Balb/3T3 cells |
| human histiocytic leukemia | rat, hamster fibroblasts |
| mouse epidermal cells | human smooth muscle cells |
| rat colonic epithelial cells | rat vascular smooth muscle cells |
| rat vascular smooth muscle cells | |

While non-transformed cells can respond to growth factors and cytokines with the production of ROI, tumor cells appear to produce ROI in an uncontrolled manner. A series of human tumor cells produced large amounts of hydrogen peroxide compared with non-tumor cells (Szatrowski et al. (1991) *Canc. Res.* 51, 794-798). Ras-transformed NIH 3T3 cells generated elevated amounts of superoxide, and inhibition of superoxide generation by several mechanisms resulted in a reversion to a "normal" growth phenotype.

$O_2^-$ has been implicated in maintenance of the transformed phenotype in cancer cells including melanoma, breast carcinoma, fibrosarcoma, and virally transformed tumor cells. Decreased levels of the manganese form of SOD (MnSOD) have been measured in cancer cells and in vitro-transformed cell lines, predicting increased $O_2^-$ levels (Burdon, R. (1995) *Free Radical Biol. Med.* 18, 775-794). MnSOD is encoded on chromosome 6q25 which is very often lost in melanoma. Overexpression of MnSOD in melanoma and other cancer cells (Church et al. (1993) *Proc. of Natl. Acad. Sci.* 90, 3113-3117; Fernandez-Pol et al. (1982) *Canc. Res.* 42, 609-617; Yan et al. (1996) *Canc. Res.* 56, 2864-2871) resulted in suppression of the transformed phenotype.

ROI are implicated in the growth of vascular smooth muscle associated with hypertension, atherosclerosis, and restenosis after angioplasty. $O_2^-$ generation is seen in rabbit aortic adventitia (Pagano et al. (1997) *Proc. Natl. Acad. Sci.* 94, 14483-14488). Vascular endothelial cells release $O_2^-$ in response to cytokines (Matsubara et al. (1986) *J. Immun.* 137, 3295-3298). $O_2^-$ is generated by aortic smooth muscle cells in culture, and increased $O_2^-$ generation is stimulated by angiotensin II which also induces cell hypertrophy. In a rat model system, infusion of angiotensin II leads to hypertension as well as increased $O_2^-$ generation in subsequently isolated aortic tissue (Ushio-Fukai et al. (1996) *J. Biol. Chem.* 271, 23317-23321; Yu et al. (1997) *J. Biol. Chem.* 272, 27288-27294). Intravenous infusion of a form of SOD that localizes to the vasculature or an infusion of an $O_2^-$ scavenger prevented angiotensin II induced hypertension and inhibited ROI generation (Fukui et al. (1997) *Circ. Res.* 80, 45-51).

The neutrophil NADPH oxidase, also known as phagocyte respiratory burst oxidase, provides a paradigm for the study of the specialized enzymatic ROI-generating system. This extensively studied enzyme oxidizes NADPH and reduces oxygen to form $O_2^-$. NADPH oxidase consists of multiple proteins and is regulated by assembly of cytosolic and membrane components. The catalytic moiety consists of flavocytochrome $b_{558}$, an integral plasma membrane enzyme comprised of two components: gp91phox (gp refers to glycoprotein; phox is an abbreviation of the words phagocyte and oxidase) and p22phox (p refers to protein). gp91phox contains 1 flavin adenine dinucleotide (FAD) and 2 hemes as well as the NADPH binding site. p22phox has a C-terminal proline-rich sequence which serves as a binding site for cytosolic regulatory proteins. The two cytochrome subunits, gp91phox and p22phox appear to stabilize one another, since the genetic absence of either subunit, as in the inherited disorder chronic granulomatous disease (CGD), results in the absence of the partner subunit (Yu et al. (1997) *J. Biol. Chem.* 272, 27288-27294). Essential cytosolic proteins include p47phox, p67phox and the small GTPase Rac, of which there are two isoforms. p47phox and p67phox both contain $SH_3$ regions and proline-rich regions which participate in protein interactions governing assembly of the oxidase components during activation. The neutrophil enzyme is regulated in response to bacterial phagocytosis or chemotactic signals by phosphorylation of p47phox, and perhaps other components, as well as by guanine nucleotide exchange to activate the GTP-binding protein Rac.

The origin of ROI in non-phagocytic tissues is unproven, but the occurrence of phagocyte oxidase components has been evaluated in several systems by immunochemical methods, Northern blots and reverse transcriptase-polymerase chain reaction (RT-PCR). The message for p22phox is expressed widely, as is that for Rac1. Several cell types that are capable of $O_2^-$ generation have been demonstrated to contain all of the phox components including gp91phox, as summarized below in Table 3. These cell types include endothelial cells, aortic adventitia and lymphocytes.

TABLE 3

| Tissue | gp91phox | p22phox | p47phox | p67phox |
| --- | --- | --- | --- | --- |
| neutrophil | +[1,2] | +[1,2] | +[1,2] | +[1,2] |
| aortic adventitia | +[1] | +[1] | +[1] | +[1] |
| lymphocytes | +[2] | +[2] | +[1,2] | +[1,2] |
| endothelial cells | +[2] | +[2] | +[1,2] | +[1,2] |
| glomerular mesangial cells | – | +[1,2] | +[1,2] | +[1,2] |
| fibroblasts | – | +[2] | +[1,2] | +[2] |
| aortic sm. muscle | – | +[1,2] | ? | ? |

[1]= protein expression shown.
[2]= mRNA expression shown.

However, a distinctly different pattern is seen in several other cell types shown in Table 3 including glomerular mesangial cells, rat aortic smooth muscle and fibroblasts. In these cells, expression of gp91phox is absent while p22phox and in some cases cytosolic phox components have been demonstrated to be present. Since gp91phox and p22phox stabilize one another in the neutrophil, there has been much speculation that some molecule, possibly related to gp91phox, accounts for ROI generation in glomerular mesangial cells, rat aortic smooth muscle and fibroblasts (Ushio-Fukai et al. (1996) *J. Biol. Chem.* 271, 23317-23321). Investigation of fibroblasts from a patient with a genetic absence of gp91phox provides proof that the gp91phox subunit is not involved in ROI generation in these cells (Emmendorffer et al. (1993) *Eur. J. Haematol.* 51, 223-227). Depletion of p22phox from vascular smooth muscle using an antisense approach indicated that this subunit participates in ROI generation in these cells, despite the absence of detectable gp91phox (Ushio-Fukai et al. (1996) *J. Biol. Chem.* 271, 23317-23321). At this time the molecular candidates possibly related to gp91phox and involved in ROI generation in these cells are unknown.

Accordingly, what is needed is the identity of the proteins involved in ROI generation, particularly in non-phagocytic tissues and cells. What is also needed are the nucleotide sequences encoding for these proteins, and the primary sequences of the proteins themselves. Also needed are vectors designed to include nucleotides encoding for these proteins. Probes and PCR primers derived from the nucleotide sequence are needed to detect, localize and measure nucleotide sequences, including mRNA, involved in the synthesis of these proteins. In addition, what is needed is a means to transfect cells with these vectors. What is also needed are expression systems for production of these molecules. Also needed are antibodies directed against these molecules for a variety of uses including localization, detection, measurement and passive immunization.

SUMMARY OF THE INVENTION

The present invention solves the problems described above by providing a novel family of nucleotide sequences and proteins, termed Nox proteins, encoded by these nucleotide sequences. In particular the present invention provides compositions comprising the nucleotide sequences SEQ ID NO:1, SEQ ID NO:3, or SEQ ID NO:5, and conservative substitutions and fragments thereof, wherein SEQ ID NO:1 and fragments thereof code for the expression of the protein comprising SEQ ID NO:2 and fragments thereof; and SEQ ID NO:3 and fragments thereof code for the expression of the protein comprising SEQ ID NO:4 and fragments thereof. SEQ ID NO:5 is the promoter sequence for Nox 1. While not wanting to be bound by the following statement, it is believed that these Nox proteins, SEQ ID NOs: 2 and 4, and fragments thereof, are involved in ROI production. The present invention also provides vectors containing these nucleotide sequences, cells transfected with these vectors which produce the proteins comprising SEQ ID NO:2 and SEQ ID NO:4, or fragments thereof, and antibodies to these proteins and fragments thereof. The present invention also provides methods for stimulating cellular proliferation by administering vectors encoded for production of the proteins comprising SEQ ID NO:2 or SEQ ID NO:4, and fragments thereof. The present invention further provides methods for stimulating cellular proliferation by administering the proteins comprising SEQ ID NO:2 or SEQ ID NO:4, and fragments thereof. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement.

Most particularly, the present invention involves a method for regulation of cell division or cell proliferation by modifying the activity or expression of the proteins described as SEQ ID NO:2 or SEQ ID NO:4, or fragments thereof. These proteins, in their naturally occurring or expressed forms, are expected to be useful in drug development, for example for screening of chemical and drug libraries by observing inhibition of the activity of these enzymes. Such chemicals and drugs would likely be useful as treatments for cancer, prostatic hypertrophy, benign prostatic hypertrophy, hypertension, atherosclerosis and many other disorders involving abnormal cell growth or proliferation as described below. The entire expressed protein may be useful in these assays. Portions of the molecule which may be targets for inhibition or modification include, but are not limited to, the binding site for pyridine nucleotides (NADPH or NADH), the flavoprotein domain (approximately the C-terminal 265 amino acids), and/or the binding or catalytic site for flavin adenine dinucleotide (FAD).

The present invention further comprises the creation of reporter-promoter constructs for use in assays to measure the activity of compounds. The method of the present invention may additionally be used for the development of drugs or other therapies for the treatment of conditions associated with abnormal growth including, but not limited to, cancer, psoriasis, prostatic hypertrophy, benign prostatic hypertrophy, cardiovascular disease, proliferation of vessels, including but not limited to blood vessels and lymphatic vessels, arteriovenous malformation, vascular problems associated with the eye, atherosclerosis, hypertension, and restenosis following angioplasty. The enzymes of the present invention are excellent targets for the development of drugs and other agents which may modulate the activity of these enzymes. It is to be understood that modulation of activity may result in enhanced, diminished or absence of enzymatic activity. Modulation of the activity of these enzymes may be useful in treatment of conditions associated with abnormal growth.

Drugs which affect the activity of the enzymes represented in SEQ ID NO:2, SEQ ID NO:4, or fragments thereof, may also be combined with other therapeutics in the treatment of specific conditions. For example, these drugs may be combined with angiogenesis inhibitors in the treatment of cancer, with antihypertensives for the treatment of hypertension, and with cholesterol lowering drugs for the treatment of atherosclerosis.

Accordingly, an object of the present invention is to provide nucleotide sequences, or fragments thereof, encoding for the production of proteins, or fragments thereof, that are involved in ROI production.

Another object of the present invention is to provide vectors containing these nucleotide sequences, or fragments thereof.

Yet another object of the present invention is to provide cells transfected with these vectors.

Still another object of the present invention is to administer cells transfected with these vectors to animals and humans.

Another object of the present invention is to provide proteins, or fragments thereof, that are involved in ROI production.

Still another object of the present invention is to provide antibodies, including monoclonal and polyclonal antibodies, or fragments thereof, raised against proteins, or fragments thereof, that are involved in ROI production.

Another object of the present invention is to administer genes containing nucleotide sequences, or fragments thereof, encoding for the production of proteins, or fragments thereof, that are involved in ROI production, to animals and humans, and also to cells obtained from animals and humans.

Another object of the present invention is to administer antisense complimentary sequences of genes containing nucleotide sequences, or fragments thereof, encoding for the production of proteins, or fragments thereof, that are involved in ROI production, to animals and humans and also to cells obtained from animals and humans.

Yet another object of the present invention is to provide a method for stimulating or inhibiting cellular proliferation by administering vectors containing nucleotide sequences, or fragments thereof, encoding for the production of proteins, or fragments thereof, that are involved in ROI production, to animals and humans. It is also an object of the present invention to provide a method for stimulating or inhibiting cellular proliferation by administering vectors containing antisense complimentary sequences of nucleotide sequences, or fragments thereof, encoding for the production of proteins, or fragments thereof, that are involved in ROI production, to animals and humans. These methods of stimulating cellular proliferation are useful for a variety of purposes, including but not limited to, developing animal models of tumor formation, stimulating cellular proliferation of blood marrow cells following chemotherapy or radiation, or in cases of anemia.

Still another object of the present invention is to provide antibodies useful in immunotherapy against cancers expressing the proteins represented in SEQ ID NO:2, SEQ ID NO:4, or fragments thereof.

Yet another object of the present invention is to provide nucleotide probes useful for the detection, localization and measurement of nucleotide sequences, or fragments thereof, encoding for the production of proteins, or fragments thereof, that are involved in ROI production.

Another object of the present invention is to provide antibodies useful for the detection, localization and measurement of nucleotide sequences, or fragments thereof, encoding for the production of proteins, or fragments thereof, that are involved in ROI production.

Another object of the present invention is to provide kits useful for detection of nucleic acids including the nucleic acids including the nucleic acids represented in SEQ ID NO:1, SEQ ID NO:3, or fragments thereof, that encode for proteins, or fragments thereof, that are involved in ROI production.

A further object of the present invention is to provide kits useful for detection of nucleic acids including nucleic acids represented in SEQ ID NO:5, or fragments thereof, representing the promoter region of Nox 1.

Still another object of the present invention is to provide kits useful for the localization of nucleic acids including the nucleic acids represented in SEQ ID NO:1, SEQ ID NO:3, or fragments thereof, that encode for proteins, or fragments thereof that are involved in ROI production.

Yet another object of the present invention is to provide kits useful for the localization of nucleic acids including the nucleic acids represented in SEQ ID NO:5 or fragments thereof, representing the promoter region of Nox 1.

Another object of the present invention is to provide kits useful for detection of proteins, including the proteins represented in SEQ ID NO:2 and SEQ ID NO:4, or fragments thereof, that are involved in ROI production.

Yet another object of the present invention is to provide kits useful for detection and measurement of proteins, including the proteins represented in SEQ ID NO:2 and SEQ ID NO:4, or fragments thereof, that are involved in ROI production.

Still another object of the present invention is to provide kits useful for localization of proteins, including the proteins represented in SEQ ID NO:2 and SEQ ID NO:4, or fragments thereof, that are involved in ROI production.

Yet another object of the present invention is to provide kits useful for the detection, measurement or localization of nucleic acids, or fragments thereof, encoding for proteins, or fragments thereof, that are involved in ROI production, for use in diagnosis and prognosis of abnormal cellular proliferation related to ROI production.

Another object of the present invention is to provide kits useful for the detection, measurement or localization of proteins, or fragments thereof, that are involved in ROI production, for use in diagnosis and prognosis of abnormal cellular proliferation related to ROI production.

A further object of the present invention is to use the proteins represented in SEQ ID NO:2 and SEQ ID NO:4, or fragments thereof, to screen for drugs that regulate the cellular levels or activity of proteins in the Nox family.

These and other objects, features and advantages of the present invention will become apparent after a review of the following detailed description of the disclosed embodiments and the appended drawings.

DETAILED DESCRIPTION OF THE INVENTION

Figure 1:
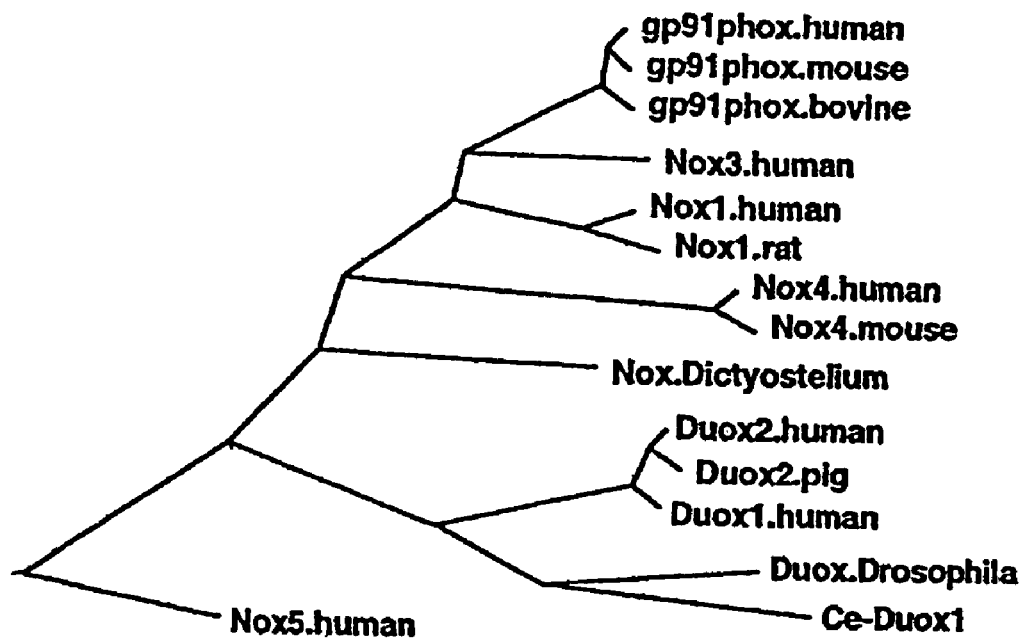
FIG. 1 is a dendrogram indicating the degree of similarity among this family of proteins, and also includes the related plant enzymes.

The present invention solves the problems described above by providing a novel family of nucleotide sequences, and proteins termed Nox proteins, encoded by these nucleotide sequences. The term "Nox" refers to "NADPH-oxidase." These novel proteins are part of a larger related family of proteins that generate ROI, including mox proteins (mox is an abbreviation for mitogenic NADPH oxidase), and Duox proteins, (duox is an abbreviation for dual oxidase). In particular, the present invention provides novel compositions comprising the nucleotide sequences SEQ ID NO:1, SEQ ID NO:3, or SEQ ID NO:5, and fragments thereof. SEQ ID NO:1, or fragments thereof, encode for proteins comprising SEQ ID NO:2 or fragments thereof. SEQ ID NO:3, or fragments thereof, encode for proteins comprising SEQ ID NO:4 or fragments thereof. SEQ ID NO:5 is the promoter region for Nox 1.

The Nox proteins described herein have homology to the gp91phox protein involved in ROI generation, however, the Nox proteins comprise a novel and distinct family of proteins. The Nox proteins included in the present invention have a molecular weight of approximately 65 kDa as determined by reducing gel electrophoresis and are capable of inducing ROI generation in cells. As described in detail below, the Nox proteins of the present invention also function in the regulation of cell growth, and are therefore implicated in diseases involving abnormal cell growth such as cancer. The present invention describes Nox proteins found in humans, however, it is likely that the Nox family of genes/proteins is widely distributed among multicellular organisms.

In addition to the nucleotide sequences described above, the present invention also provides vectors containing these nucleotide sequences and fragments thereof, cells transfected with these vectors which produce the proteins comprising SEQ ID NO:2, SEQ ID NO:4, and fragments thereof, and antibodies to these proteins and fragments thereof. The present invention also provides methods for stimulating cellular proliferation by administering vectors, or cells containing vectors, encoded for production of the proteins comprising SEQ ID NO:2, SEQ ID NO:4, and fragments thereof. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement. These kits are useful for diagnosis and prognosis of conditions involving cellular proliferation associated with production of reactive oxygen intermediates.

The present invention solves the problems described above by providing a composition comprising the nucleotide sequence SEQ ID NO:1 and fragments thereof. The present invention also provides a composition comprising the nucleotide sequence SEQ ID NO:3 and fragments thereof. The present invention additionally provides a composition comprising the nucleotide sequence SEQ ID NO: 5 and fragments thereof.

The present invention provides a composition comprising the protein SEQ ID NO:2 encoded by the nucleotide sequence SEQ ID NO:1. The present invention additionally provides a composition comprising the protein SEQ ID NO:4 encoded by the nucleotide sequence SEQ ID NO:3.

The present invention provides a composition comprising the protein SEQ ID NO:2 or fragments thereof, encoded by the nucleotide sequence SEQ ID NO:1 or fragments thereof. The present invention also provides a composition comprising the protein SEQ ID NO:4 or fragments thereof, encoded by the nucleotide sequence SEQ ID NO:3 or fragments thereof.

The present invention also provides vectors containing the nucleotide sequences SEQ ID NO:1, SEQ ID NO:3, or SEQ ID NO:5, and fragments thereof. The present invention also provides cells transfected with these vectors. In addition, the present invention provides cells stably transfected with the nucleotide sequence SEQ ID NO:1 or fragments thereof. The present invention also provides cells stably transfected with the nucleotide sequence SEQ ID NO:3 or fragments thereof.

The present invention provides cells stably transfected with the nucleotide sequence SEQ ID NO:1 or fragments thereof, which produce the protein SEQ ID NO:2 or fragments thereof. In addition, the present invention provides cells stably transfected with the nucleotide sequence SEQ ID NO:3 or fragments thereof which produce the protein SEQ ID NO:4 or fragments thereof.

The present invention provides a method for stimulating growth by administering cells stably transfected with the nucleotide sequence SEQ ID NO:1 which produce the protein SEQ ID NO:2 or fragments thereof. The present invention also provides a method for stimulating growth by administering cells stably transfected with the nucleotide sequence SEQ ID NO:3 or fragments thereof, which produce the protein SEQ ID NO:4 or fragments thereof.

Specifically, the present invention provides a method for stimulating tumor formation by administering cells stably transfected with the nucleotide sequence SEQ ID NO:1 or fragments thereof, which produce the protein SEQ ID NO:2 or fragments thereof. The present invention also provides a method for stimulating tumor formation by administering cells stably transfected with the nucleotide sequence SEQ ID NO:3 or fragments thereof, which produce the protein SEQ ID NO:4 or fragments thereof.

The present invention may also be used to develop anti-sense nucleotide sequences to SEQ ID NO:1, SEQ ID NO:3, or SEQ ID NO:5, or fragments thereof. These anti-sense molecules may be used to interfere with translation of nucleotide sequences, such as SEQ ID NO:1, or SEQ ID NO:3, or fragments thereof, that encode respectively, for proteins such as SEQ ID NO:2, SEQ ID NO:4, or fragments thereof. Administration of these anti-sense molecules, or vectors encoding for these anti-sense molecules, to humans and animals, would interfere with production of proteins such as SEQ ID NO:2, SEQ ID NO:4, or fragments thereof, thereby decreasing production of ROIs and inhibiting cellular proliferation. These methods are useful in producing animal models for use in study of tumor development and vascular growth, and for study of the efficacy of treatments for affecting tumor and vascular growth in vivo.

The present invention also provides a method for high throughput screening of drugs and chemicals which modulate the proliferative activity of the enzymes of the present invention, thereby affecting cell division. Combinatorial chemical libraries may be screened for chemicals which modulate the proliferative activity of these enzymes. Drugs and chemicals may be evaluated based on their ability to modulate the enzymatic activity of the expressed or endogenous proteins, including those represented by SEQ ID NO:2, SEQ ID NO:4, or fragments thereof. Endogenous proteins may be obtained from many different tissues or cells, such as colon cells. Drugs may also be evaluated based on their ability to bind to the expressed or endogenous proteins represented by SEQ ID NO:2, SEQ ID NO:4, or fragments thereof. Enzymatic activity may be NADPH- or NADH-dependent superoxide generation catalyzed by the holoprotein. Enzymatic activity may also be NADPH- or NADH-dependent diaphorase activity catalyzed by either the holoprotein or the flavoprotein domain.

By flavoprotein domain is meant approximately the C-terminal half of the enzymes shown in SEQ ID NO:2, SEQ ID NO:4, or fragments thereof. These proteins and fragments thereof have NADPH-dependent reductase activity towards cytochrome c, nitrobluetetrazolium and other dyes. Expressed proteins or fragments thereof can be used for robotic screens of existing combinatorial chemical libraries. While not wanting to be bound by the following statement, it is believed that the NADPH or NADH binding site and the FAD binding site are useful for evaluating the ability of drugs and other compositions to bind to the Nox enzymes or to modulate their enzymatic activity. The use of the holoprotein or the C-terminal half or end regions are preferred for developing a high throughput drug screen.

The present invention also provides antibodies directed to the proteins SEQ ID NO:2, SEQ ID NO:4, and fragments thereof. The antibodies of the present invention are useful for a variety of purposes including localization, detection and measurement of the proteins SEQ ID NO:2, SEQ ID NO:4, and fragments thereof. The antibodies may be employed in kits to accomplish these purposes. These antibodies may also be linked to cytotoxic agents for selected killing of cells. The term antibody is meant to include any class of antibody such as IgG, IgM and other classes. The term antibody also includes a completely intact antibody and also fragments thereof, including but not limited to Fab fragments and Fab+ Fc fragments.

The present invention also provides the nucleotide sequences SEQ ID NO:1, SEQ ID NO:3, and fragments thereof. These nucleotide sequences are useful for a variety of purposes including localization, detection, and measurement of messenger RNA involved in synthesis of the proteins represented as SEQ ID NO:2, SEQ ID NO:4, and fragments thereof. The present invention also provides the nucleotide sequence for SEQ ID NO:5 and fragments thereof. This nucleotide sequence is useful for a variety of purposes including localization, detection and measurement of messenger RNA involved in synthesis of the Nox family of proteins. These nucleotides may also be used in the construction of labeled probes for the localization, detection, and measurement of nucleic acids such as messenger RNA or alternatively for the isolation of larger nucleotide sequences containing the nucleotide sequences shown in SEQ ID NO:1, SEQ ID NO:3, SEQ ID NO:5, or fragments thereof. These nucleotide sequences may be used to isolate homologous strands from other species using techniques known to one of ordinary skill in the art. These nucleotide sequences may also be used to make probes and complementary strands.

Most particularly, the present invention involves a method for modulation of growth by modifying the proteins represented as SEQ ID NO:2, SEQ ID NO:4, or fragments thereof.

The term "mitogenic regulators" is used herein to mean any molecule that acts to affect cell division.

The term "animal" is used herein to mean humans and non-human animals of both sexes.

The terms "a", "an" and "the" as used herein are defined to mean one or more and include the plural unless the context is inappropriate.

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that, as mentioned above, individual substitutions, deletions or additions which alter, add or delete a single amino acid or a small percentage of amino acids (less than about 20%, typically less than about 10%, more typically less than about 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the antigenic epitopes described herein are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

One of skill in the art will recognize that after chemical synthesis, biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

The genetic constructs of the present invention include coding sequences for different proteins, fragments thereof, and peptides. The genetic constructs also include epitopes or domains chosen to permit purification or detection of the expressed protein. Such epitopes or domains include DNA sequences encoding the glutathione binding domain from glutathione S-transferase, hexa-histidine, thioredoxin, hemagglutinin antigen, maltose binding protein, and others commonly known to one of skill in the art. The preferred genetic construct includes the nucleotide sequences of SEQ ID NO:1, SEQ ID NO:3, or SEQ ID NO:5, or fragments thereof. It is to be understood that additional or alternative nucleotide sequences may be included in the genetic constructs in order to encode for the following: a) multiple copies of the desired proteins, fragments thereof, or peptides; b) various combinations of the desired proteins, fragments thereof, or peptides; and c) conservative modifications of the desired proteins, fragments thereof, or peptides, and combinations thereof. Preferred proteins include the human Nox 4 protein and human Nox 5 protein shown as SEQ ID NO:2 and SEQ ID NO:4, respectively, and fragments thereof or conservative substitutions thereof.

The nucleotide sequences of the present invention may also be employed to hybridize to nucleic acids such as DNA or RNA nucleotide sequences under high stringency conditions which permit detection, for example, of alternately spliced messages.

The genetic construct is expressed in an expression system such as in NIH 3T3 cells using recombinant sequences in a pcDNA-3 vector (Invitrogen, Carlsbad, Calif.) to produce a recombinant protein. Preferred expression systems include but are not limited to Cos-7 cells, insect cells using recombinant baculovirus, and yeast. It is to be understood that other expression systems known to one of skill in the art may be used for expression of the genetic constructs of the present invention. The preferred proteins of the present invention are the sequences referred to herein as human Nox 4 and human Nox 5 or fragments thereof which have the amino acid sequences set forth in SEQ ID NO:2 and SEQ ID NO:4, respectively, or an amino acid sequence having amino acid substitutions as defined in the definitions that do not significantly alter the function of the recombinant protein in an adverse manner.

Terminology

It should be understood that some of the terminology used to describe the novel Nox proteins contained herein is different from the terminology in PCT/US99/26592, U.S. nonprovisional application Ser. No. 09/437,568 and U.S. provisional application Ser. Nos. 60/251,364, 60/249,305, and 60/289,172. The terms mox and nox are equivalents. As described herein, the term "human Nox 4" refers to a protein comprising an amino acid sequence as set forth in SEQ ID NO:2, or fragments or conservative substitutions thereof, and encoded by the nucleotide sequence as set forth in SEQ ID NO:1, or fragments or conservative substitutions thereof. As described herein, the term "human Nox 5" refers to a protein comprising an amino acid sequence as set forth in SEQ ID NO:4, or fragments or conservative substitutions thereof, and encoded by the nucleotide sequence as set forth in SEQ ID NO:3, or fragments or conservative substitutions thereof. The promoter for "human Nox 1" refers to a nucleic acid sequence as set forth in SEQ ID NO:5 or fragments or conservative substitutions thereof.

Construction of the Recombinant Gene

The desired gene is ligated into a transfer vector, such as pcDNA3, and the recombinants are used to transform host cells such as Cos-7 cells. It is to be understood that different transfer vectors, host cells, and transfection methods may be employed as commonly known to one of ordinary skill in the art. Three desired genes for use in transfection are shown in SEQ ID NO:1, SEQ ID NO:3, and SEQ ID NO:5. For example, lipofectamine-mediated transfection and in vivo homologous recombination was used to introduce the Nox 4 gene (SEQ ID NO:1) into NIH 3T3 cells.

The synthetic gene is cloned and the recombinant construct containing a Nox gene is produced and grown in confluent monolayer cultures of a Cos-7 cell line. The expressed recombinant protein is then purified, preferably using affinity chromatography techniques, and its purity and specificity determined by known methods.

A variety of expression systems may be employed for expression of the recombinant protein. Such expression methods include, but are not limited to the following: bacterial expression systems, including those utilizing *E. coli* and *Bacillus subtilis*; virus systems; yeast expression systems; cultured insect and mammalian cells; and other expression systems known to one of ordinary skill in the art.

Transfection of Cells

It is to be understood that the vectors of the present invention may be transfected into any desired cell or cell line. Both in vivo and in vitro transfection of cells are contemplated as part of the present invention. Preferred cells for transfection include but are not limited to the following: fibroblasts (possibly to enhance wound healing and skin formation), granulocytes (possible benefit to increase function in a compromised immune system as seen in AIDS, and aplastic anemia), muscle cells, neuroblasts, stem cells, bone marrow cells, osteoblasts, B lymphocytes, and T lymphocytes.

Cells may be transfected with a variety of methods known to one of ordinary skill in the art and include but are not limited to the following: electroporation, gene gun, calcium phosphate, lipofectamine, and fugene, as well as adenoviral transfection systems.

Host cells transfected with the nucleic acids represented in SEQ ID NO:1, SEQ ID NO:3, or fragments thereof, are used to express the proteins SEQ ID NO:2, SEQ ID NO:4, respectively, or fragments thereof. Host cells transfected with the nucleic acid represented in SEQ ID NO:1, SEQ ID NO:3, or SEQ ID NO:5 or fragments thereof, are also used as screening assays.

These expressed proteins are used to raise antibodies. These antibodies may be used for a variety of applications including but not limited to immunotherapy against cancers expressing one of the Nox proteins, and for detection, localization and measurement of the proteins shown in SEQ ID NO:2, SEQ ID NO:4, or fragments thereof.

Purification and Characterization of the Expressed Protein

The proteins of the present invention can be expressed as a fusion protein with a poly histidine component, such as a hexa histidine, and purified by binding to a metal affinity column using nickel or cobalt affinity matrices. The protein can also be expressed as a fusion protein with glutathione S-transferase and purified by affinity chromatography using a glutathione agarose matrix. The protein can also be purified by immunoaffinity chromatography by expressing it as a fusion protein, for example with hemagglutinin antigen. The expressed or naturally occurring protein can also be purified by conventional chromatographic and purification methods which include anion and cation exchange chromatography, gel exclusion chromatography, hydroxylapatite chromatography, dye binding chromatography, ammonium sulfate precipitation, precipitation in organic solvents or other techniques commonly known to one of skill in the art.

Methods of Assessing Activity of Expressed Proteins

Different methods are available for assessing the activity of the expressed proteins of the present invention, including but not limited to the proteins represented as SEQ ID NO:2, SEQ ID NO:4, conservative substitutions thereof, and fragments thereof.

1. Assays of the Holoprotein and Fragments Thereof for Superoxide Generation

A. General Considerations.

These assays are useful in assessing efficacy of drugs designed to modulate the activity of the enzymes of the present invention. The holoprotein may be expressed in COS-7 cells, NIH 3T3 cells, insect cells (using baculoviral technology) or other cells using methods known to one of skill in the art. Membrane fractions or purified protein are used for the assay. The assay may require or be augmented by other cellular proteins such as p47phox, p67phox, and Rac1, as well as potentially other unidentified factors (e.g., kinases or other regulatory proteins).

B. Cytochrome c Reduction.

NADPH or NADH is used as the reducing substrate, in a concentration of about 100 µM. Reduction of cytochrome c is monitored spectrophotometrically by the increase in absorbance at 550 nm, assuming an extinction coefficient of 21 $mM^{-1}$ $cm^{-1}$. The assay is performed in the absence and presence of about 10 µg superoxide dismutase. The superoxide-dependent reduction is defined as cytochrome c reduction in the absence of superoxide dismutase minus that in the presence of superoxide dismutase (Uhlinger et al. (1991) *J. Biol. Chem.* 266, 20990-20997). Acetylated cytochrome c may also be used, since the reduction of acetylated cytochrome c is thought to be exclusively via superoxide.

C. Nitroblue Tetrazolium Reduction.

For nitroblue tetrazolium (NBT) reduction, the same general protocol is used, except that NBT is used in place of cytochrome c. In general, about 1 mL of filtered 0.25% nitrotetrazolium blue (Sigma, St. Louis, Mo.) is added in Hanks buffer without or with about 600 Units of superoxide dismutase (Sigma) and samples are incubated at approximately 37° C. The oxidized NBT is clear, while the reduced NBT is blue and insoluble. The insoluble product is collected by centrifugation, and the pellet is re-suspended in about 1 mL of pyridine (Sigma) and heated for about 10 minutes at 100° C. to solubilize the reduced NBT. The concentration of reduced NBT is determined by measuring the absorbance at 510 nm, using an extinction coefficient of 11,000 $M^{-1}$ $cm^{-1}$. Untreated wells are used to determine cell number.

D. Luminescence.

Superoxide generation may also be monitored with a chemiluminescence detection system utilizing lucigenin (bis-N-methylacridinium nitrate, Sigma, St. Louis, Mo.). The sample is mixed with about 100 µM NADPH (Sigma, St. Louis, Mo.) and 10 µM lucigenin (Sigma, St. Louis, Mo.) in a volume of about 150 µL Hanks solution. Luminescence is monitored in a 96-well plate using a LumiCounter (Packard, Downers Grove, Ill.) for 0.5 second per reading at approximately 1 minute intervals for a total of about 5 minutes; the highest stable value in each data set is used for comparisons. As above, superoxide dismutase is added to some samples to prove that the luminescence arises from superoxide. A buffer blank is subtracted from each reading (Ushio-Fukai et al. (1996) *J. Biol. Chem.* 271, 23317-23321).

E. Assays in Intact Cells.

Assays for superoxide generation may be performed using intact cells, for example, the Nox-transfected NIH 3T3 cells. In principle, any of the above assays can be used to evaluate superoxide generation using intact cells, for example, the Nox-transfected NIH 3T3 cells. NBT reduction is a preferred assay method.

2. Assays of Truncated Proteins Comprised of Approximately the C-terminal 265 Amino Acid Residues While not wanting to be bound by the following statement, the truncated protein comprised of approximately the C-terminal 265 amino acid residues is not expected to generate superoxide, and therefore, superoxide dismutase is not added in assays of the truncated protein. Basically, a similar assay is established and the superoxide-independent reduction of NBT, cytochrome c, dichlorophenolindophenol, ferricyanide, or another redox-active dye is examined.

Nucleotides and Nucleic Acid Probes

The nucleotide sequences SEQ ID NO:1, SEQ ID NO:3, SEQ ID NO:5, as well as fragments thereof and PCR primers therefore, may be used, respectively, for localization, detection and measurement of nucleic acids related to SEQ ID NO:1, SEQ ID NO:3, SEQ ID NO:5, as well as fragments thereof. The nucleotide sequences SEQ ID NO:1 and SEQ ID NO:3 are also called the human Nox 4 gene and the human Nox 5 gene respectively, in this application. The nucleotide sequence SEQ ID NO:5 is called the Nox 1 promoter sequence in this application.

The nucleotide sequences SEQ ID NO:1, SEQ ID NO:3, SEQ ID NO:5, as well as fragments and conservative substitutions thereof, may be used to create probes to isolate larger nucleotide sequences containing the nucleotide sequences SEQ ID NO:1, SEQ ID NO:3, and SEQ ID NO:5, respectively. The nucleotide sequences SEQ ID NO:1, SEQ ID NO:3, and SEQ ID NO:5 as well as fragments thereof and conservative substitutions thereof, may also be used to create probes to identify and isolate Nox proteins in other species.

The nucleic acids described herein include messenger RNA coding for production of SEQ ID NO:2, SEQ ID NO:4, and fragments and conservative substitutions thereof. Such nucleic acids include but are not limited to cDNA probes. These probes may be labeled in a variety of ways known to one of ordinary skill in the art. Such methods include but are not limited to isotopic and non-isotopic labeling. These probes may be used for in situ hybridization for localization of nucleic acids such as mRNA encoding for SEQ ID NO:2, SEQ ID NO:4, and fragments and conservative substitutions thereof. Localization may be performed using in situ hybridization at both ultrastructural and light microscopic levels of resolution using techniques known to one of ordinary skill in the art.

These probes may also be employed to detect and quantitate nucleic acids and mRNA levels using techniques known to one of ordinary skill in the art including but not limited to solution hybridization.

Administration of the Nox Proteins of the Present Invention

The proteins represented by SEQ ID NO:2, or SEQ ID NO:4, or fragments or conservative substitutions thereof, are combined with a pharmaceutically acceptable carrier or vehicle to produce a pharmaceutical composition and are administered to animals. Such administration may occur for stimulation of growth or cellular proliferation. Administration may also occur for generation of antibodies.

The terms "pharmaceutically acceptable carrier or pharmaceutically acceptable vehicle" are used herein to mean any liquid including but not limited to water or saline, oil, gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The pharmaceutical compositions may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The pharmaceutical composition may be administered through different routes, such as oral, including buccal and sublingual, rectal, parenteral, aerosol, nasal, intramuscular, subcutaneous, intradermal, and topical. The pharmaceutical composition of the present invention may be administered in different forms, including but not limited to solutions, emulsions and suspensions, microspheres, particles, microparticles, nanoparticles, and liposomes.

The pharmaceutical composition may be stored at temperatures of from about 4° C. to −100° C. The pharmaceutical composition may also be stored in a lyophilized state at different temperatures including room temperature. The pharmaceutical composition may be sterilized through conventional means known to one of ordinary skill in the art. Such means include, but are not limited to filtration, radiation and heat. The pharmaceutical composition of the present invention may also be combined with bacteriostatic agents, such as thimerosal, to inhibit bacterial growth.

Administration may also occur for the production of polyclonal antibodies using methods known to one of ordinary skill in the art. The preferred animals for antibody production are rabbits and mice. Other animals may be employed for immunization with these proteins or fragments thereof. Such animals include, but are not limited to the following; sheep, horses, pigs, donkeys, cows, monkeys and rodents such as guinea pigs and rats. It is expected that from about 1 to 7 dosages may be required per immunization regimen. Initial injections may range from about 0.1 µg to 1 mg, with a preferred range of about 1 µg to 800 µg, and a more preferred range of from approximately 25 µg to 500 µg. Booster injections may range from 0.1 µg to 1 mg, with a preferred range of approximately 1 µg to 800 µg, and a more preferred range of about 10 µg to 500 µg.

The volume of administration will vary depending on the route of administration and the size of the recipient. For example, intramuscular injections may range from about 0.1 ml to 1.0 ml.

Adjuvants

A variety of adjuvants known to one of ordinary skill in the art may be administered in conjunction with the protein in the pharmaceutical composition for generation of antibodies. Such adjuvants include, but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; or combinations thereof.

Monoclonal antibodies can be produced using hybridoma technology in accordance with methods well known to those skilled in the art. The antibodies are useful as research or diagnostic reagents or can be used for passive immunization. The composition may optionally contain an adjuvant.

The polyclonal and monoclonal antibodies useful as research or diagnostic reagents may be employed for detection and measurement of SEQ ID NO:2, SEQ ID NO:4, and fragments or conservative substitutions thereof. Such antibodies may be used to detect these proteins in a biological sample, including but not limited to samples such as cells, cellular extracts, tissues, tissue extracts, biopsies, tumors, and biological fluids. Such detection capability is useful for detection of disease related to these proteins to facilitate diagnosis and prognosis and to suggest possible treatment alternatives.

Detection may be achieved through the use of immunocytochemistry, ELISA, radioimmunoassay or other assays as commonly known to one of ordinary skill in the art. The Nox 4 and Nox 5 proteins, or fragments or conservative substitutions thereof, may be labeled through commonly known approaches, including but not limited to the following: radiolabeling, dyes, magnetic particles, biotin-avidin, fluorescent molecules, chemiluminescent molecules and systems, ferritin, colloidal gold, and other methods known to one of skill in the art of labeling proteins.

Administration of Antibodies

The antibodies directed to the proteins shown as SEQ ID NO:2, SEQ ID NO:4, or directed to fragments or conservative substitutions thereof, may also be administered directly to humans and animals in a passive immunization paradigm. Antibodies directed to extracellular portions of SEQ ID NO:2, SEQ ID NO:4, or fragments thereof bind to these extracellular epitopes. Attachment of labels to these antibodies facilitates localization and visualization of sites of binding. Attachment of molecules such as ricin or other cytotoxins to these antibodies helps to selectively damage or kill cells expressing SEQ ID NO:2, SEQ ID NO:4, or fragments thereof.

Kits

The present invention includes kits useful with the antibodies, nucleic acid probes, labeled antibodies, labeled proteins or fragments thereof for detection, localization and measurement of SEQ ID NO: 1, SEQ ID NO:2, SEQ ID NO:3, SEQ ID NO:4, SEQ ID NO:5 or combinations thereof and fragments or conservative substitutions thereof. The diagnostic kits may also measure or detect the relative expression of the Nox proteins described herein (i.e. human Nox 4 and/or human Nox 5)

Kits may be used for immunocytochemistry, in situ hybridization, solution hybridization, radioimmunoassay, ELISA, Western blots, quantitative PCR, and other assays for the detection, localization and measurement of these nucleic acids, proteins or fragments thereof using techniques known to one of skill in the art.

The nucleotide sequences shown in SEQ ID NO:1, SEQ ID NO:3, SEQ ID NO:5, or fragments thereof, may also be used under high stringency conditions to detect alternately spliced messages related to SEQ ID NO:1, SEQ ID NO:3, SEQ ID NO:5, or fragments thereof, respectively.

Fragments of SEQ ID NO:1, SEQ ID NO:3, SEQ ID NO:5, containing the relevant hybridizing sequence can be synthesized onto the surface of a chip array. RNA samples, e.g., from tumors, are then fluorescently tagged and hybridized onto the chip for detection. This approach may be used diagnostically to characterize tumor types and to tailor treatments and/or provide prognostic information. Such prognostic information may have predictive value concerning disease progression and life span, and may also affect choice of therapy.

The other present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Sequence Analysis and Cloning of the Human Nox 4 cDNA (SEQ ID NO:1) Encoding for Production of the Human Nox 4 Protein (SEQ ID NO:2)

Using Nox 3 (SEQ ID NO:6) as a query sequence, a 789 base pair sequenced portion of expressed sequence tag (EST) (SEQ ID NO: 27) and a 408 base EST clone SEQ ID NO: 28, a clone exhibiting a 26% identity to the cDNA sequence corresponding to amino acid residues 433-560 of Nox 3, and a second clone showing 36% identity to the cDNA sequence corresponding to amino acid residues 5-48 of Nox 3 were discovered. This homologue was cloned using two PCR primers based on the two EST sequences: (SEQ ID NO:7, 5'-CAACGAAGGGGTTAAACACCTCTGC-3'; and SEQ ID NO:8, 5'-CACAGCTGATTGATTCCGCTGAG-3'). PCR was carried out using human fetal kidney marathon-ready cDNA (Clontech, Palo Alto, Calif.), and the 0.85 kb product was sequenced. Based on the sequencing results, 5'- and 3'-RACE using the same library using the following primers: 5'-RACE: SEQ ID NO:9, 5'-TAAGCCAAGAGTGTTCG-GCACATG-3'; SEQ ID NO:10, 5'-TACTCTGGCCCTTG-GTTATACAGCA-3'(for nested PCR); 3'-RACE: SEQ ID NO:11, 5'-TCCATTTACCCTCACAATGTGT-3'; SEQ ID NO:12, 5'-CTCAGCGGAATCAATCAGCTGTG-3'(for nested PCR) was then carried out. PCR parameters were 95° C. for 30s, 62° C. or 65° C. for 20s, 72° C. for 45s 25-35 cycles as indicated after denaturing for, 1 min 30s at 95° C. PCR products were purified with a QIAquick PCR purification kit or a gel purification kit (QIAGEN, Valencia, Calif.). The positive PCR bands were sequenced by ABI 377 automatic sequencing. Primers were designed to subclone the full-length cDNA and the correct sequence was confirmed by automated sequencing.

Secretion signal sequences were predicted according to web-based SMART program (version 3.1) at EMBL (Heidelberg, Germany). Prediction of open reading frames (ORF) was carried out using the EditSeq program (DNASTAR), and phylogenetic analyses and multiple sequence alignment were carried out using the clustal method using the Megalign program (DNASTAR). Transmembrane alpha helices were predicted using the TMHMM algorithms through the Center for Biological Sequence Analysis (Lyngby, Denmark).

Total RNA was extracted from cell lines with Trizol (Life Technologies, Gaithersburg, Md.) based on the manufacturer's protocol or according to (Ishii et al., 1999) for glioma cell lines. RNAs were reverse transcribed into first-strand cDNA with Superscript II (Life Technologies, Gaithersburg, Md.) using oligo-dT according on the method provided by the manufacturer.

Figure 2A:
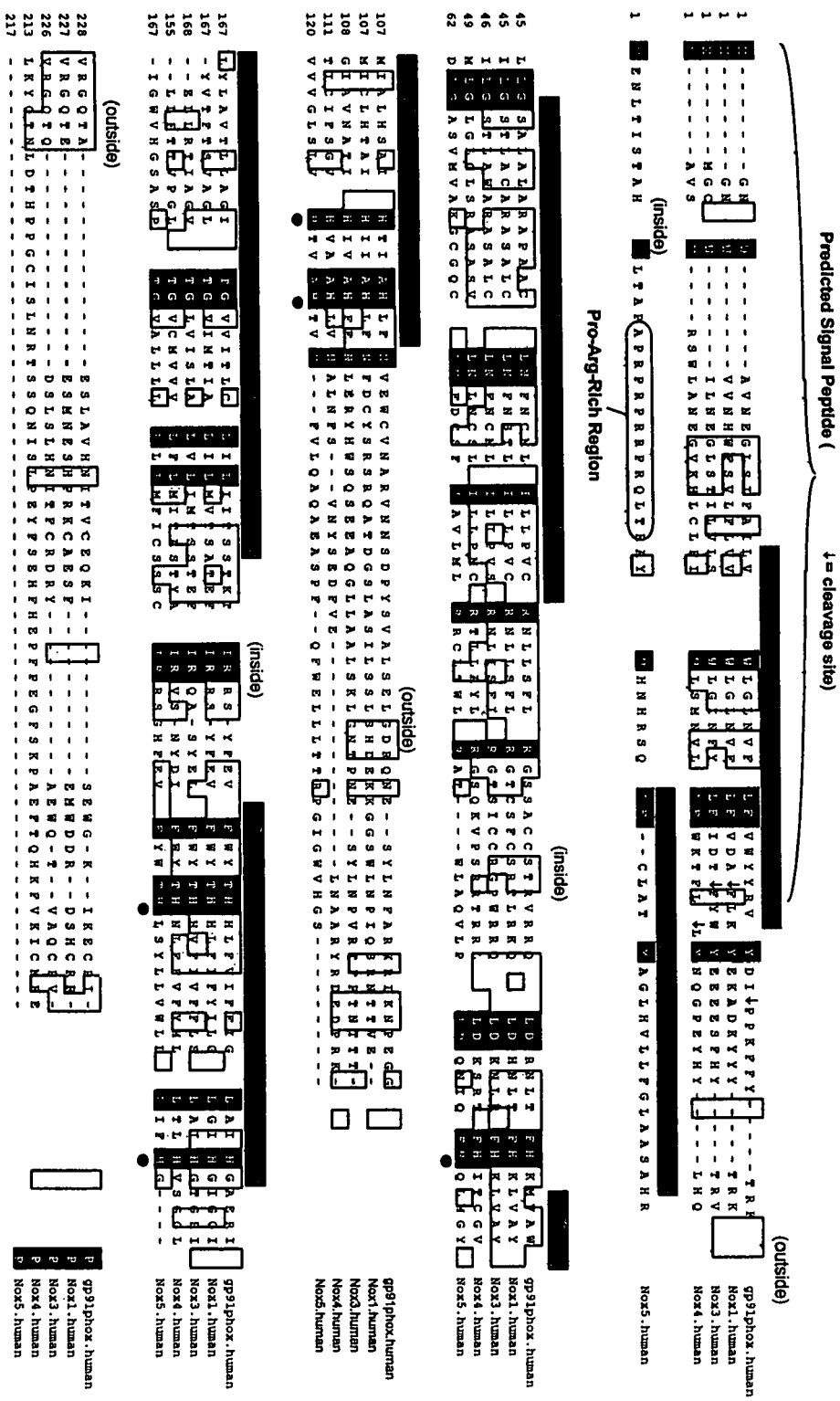
FIG. 2(*a-b*) depicts the alignment of the predicted protein sequences of gp91phox, Nox 1, Nox 3, Nox 4 and Nox 5.
Figure 2B:
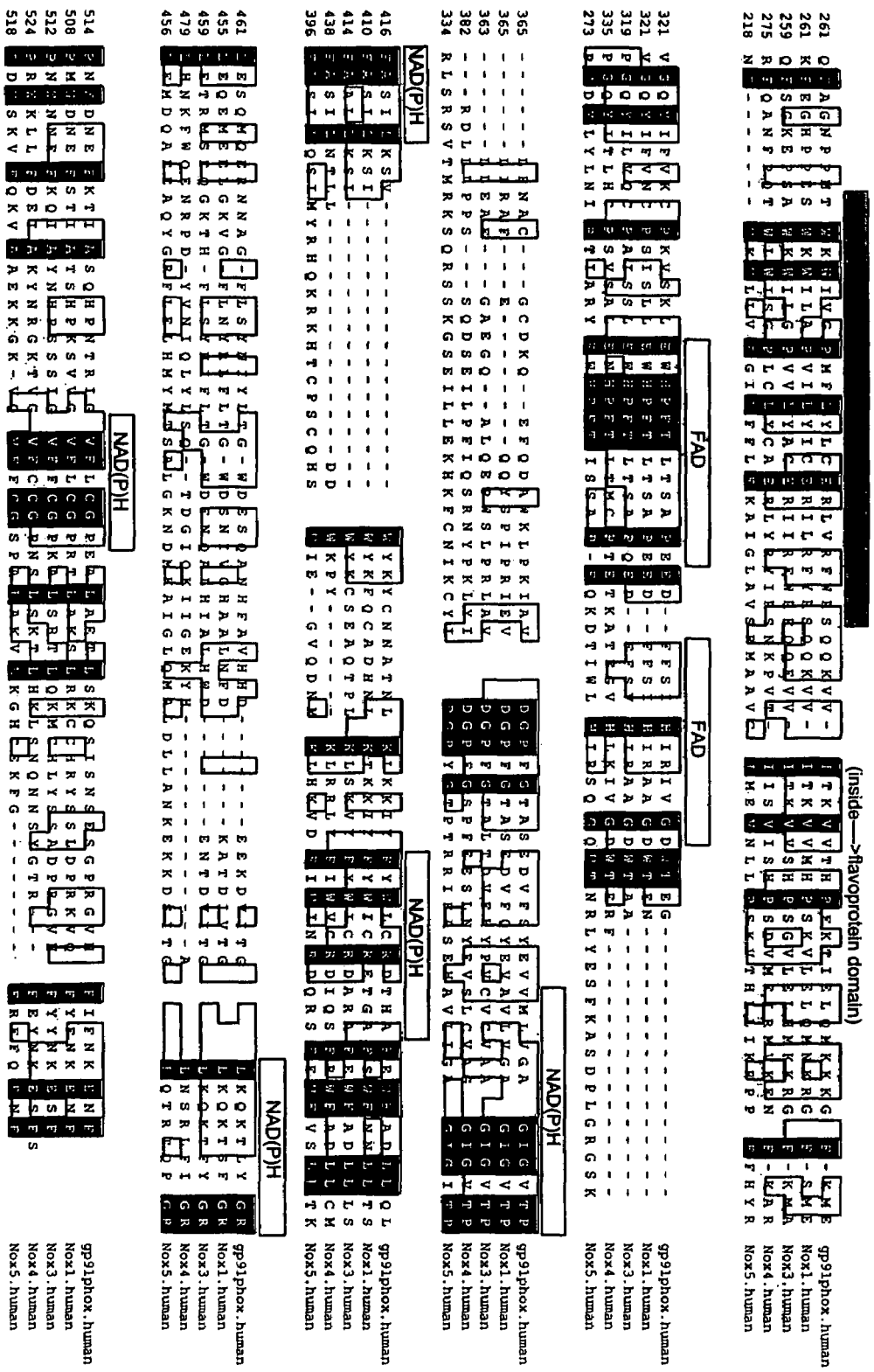

Table 4 shows the basic features of the cDNA and the predicted proteins. Like the proteins encoded by gp91phox (a.k.a., Nox 2 SEQ ID NO:13) and Nox 1 (SEQ ID NO:14), the new sequences encode predicted proteins of around 65 kDa, and message sizes are similar in length (2.0-2.2 kb). Nox 4 also has 59 amino acids which are strongly basic, 45 amino acids which are strongly acidic, 212 hydrophobic amino acids, 171 polar amino acids, an isoelectric point of 8.695 and a charge of 16.549 at a pH of 7.0. Nox 4 also shows 21-59% identity with gp91phox and with Nox 1. Nox 1, gp91phox, Nox 3 and Nox 4 cluster within a sub-family that is similar to gp91phox. The alignment of the predicted protein sequence of Nox 4 is shown in FIG. 2. The molecules are roughly divided into two large domains: an N-terminal cluster of hydrophobic membrane-spanning sequences, and a C-terminal flavoprotein domain. The latter shows weak homology with a number of FAD binding proteins including cytochrome P-450 reductase and ferredoxin-NADP oxidoreductase (Rotrosen et al., 1992; Segal et al., 1992). Within the flavoprotein domain are two segments (indicated in FIG. 2(a-b)) that show homology with known FAD binding sites in other flavoproteins, and four segments closer to the C-terminus that are homologous to documented pyridine nucleotide binding sites in other proteins. The first of these includes the G-X-G-X-X-P canonical sequence that characterizes pyridine nucleotide binding sites. In all Nox forms, this sequence is followed by an F, which is typical of NADPH-rather than NADH-specific enzymes.

Nox 4 contains the predicted transmembrane alpha helix near the extreme N-terminus (light hashed box in FIG. 2). However, this region is also strongly predicted to be a signal peptide sequence in these forms. Predicted proteolytic cleavage sites for each isoform are indicated by the arrows, and cleavage at these positions would lead to a loss of the first putative transmembrane sequence. Five additional transmembrane regions are also predicted in this protein. The most C-terminal of these is weakly predicted in Nox 1, gp91phox, Nox 3 and Nox 4 and is entirely missed by some prediction algorithms. It is necessary to include this transmembrane region in order to generate a model (FIG. 3) which is consistent with known features of gp91phox, particularly a cytosolic facing location of the flavoprotein domain. In this model, known N-linked glycosylation sites in gp91phox are correctly localized to extracellular loops (although these sites are not conserved in other isoforms). In addition, a polybasic loop of gp91phox that binds to the cytosolic regulatory protein p47phox (Biberstine-Kinkade et al., 1999) is localized on the cytosolic face. In general, extracellular loops tend to be highly variable in length and sequence, whereas the transmembrane helices and intracellular loops tend to be more conserved in sequence and length (FIG. 2).

Figure 3:
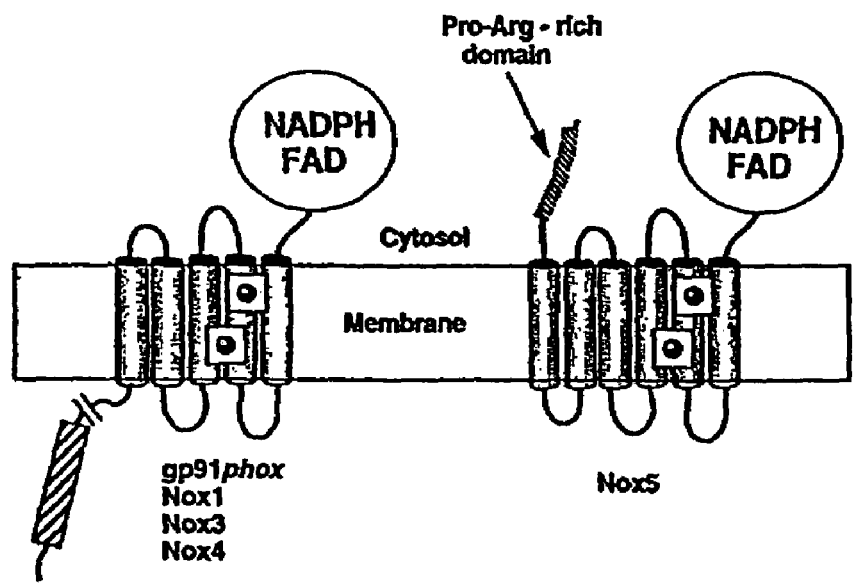
FIG. 3 is a model consistent with the known features of gp91phox.

Within the N-terminus are five absolutely conserved histidines (FIG. 2), that are also conserved in all other members of the Nox family of enzymes. gp91phox contains two heme groups, the irons of which are each ligated by two histidyl nitrogens (Isogai et al., 1993), and these are thought to reside within the N-terminus (Yu et al., 1998). An additional conserved histidine lies within the FAD-binding region and is therefore not a candidate for heme ligation. Thus, four of the five histidines within the N-terminus probably participate in heme ligation, providing part of the binding sites for two heme groups, as indicated in FIG. 3.

TABLE 4

Molecular Features of Nox 3, Nox 4, and Nox 5 cDNA

|  | Nox 3 | Nox 4 | Nox 5 |
|---|---|---|---|
| cDNA length (bp) | 2044 | 2232 | 2199 |
| Predicted number of amino acids | 568 | 578 | 565 |
| Predicted protein Mw (kDa) | 64.9 | 66.9 | 64.7 |
| pI of protein | 8 | 8.7 | 9.7 |
| Kozak sequence | ATCATGA or ATGATGG | GGCATGG | GTCATGG |
| Identity to gp91phox | 58% | 37% | 27% |
| Identity to NoxI | 55% | 35% | 29% |
| SEQ ID NO: | 29 | 30 | 31 |

EXAMPLE 2

Tissue Expression of Nox 4 mRNA

Figure 4:
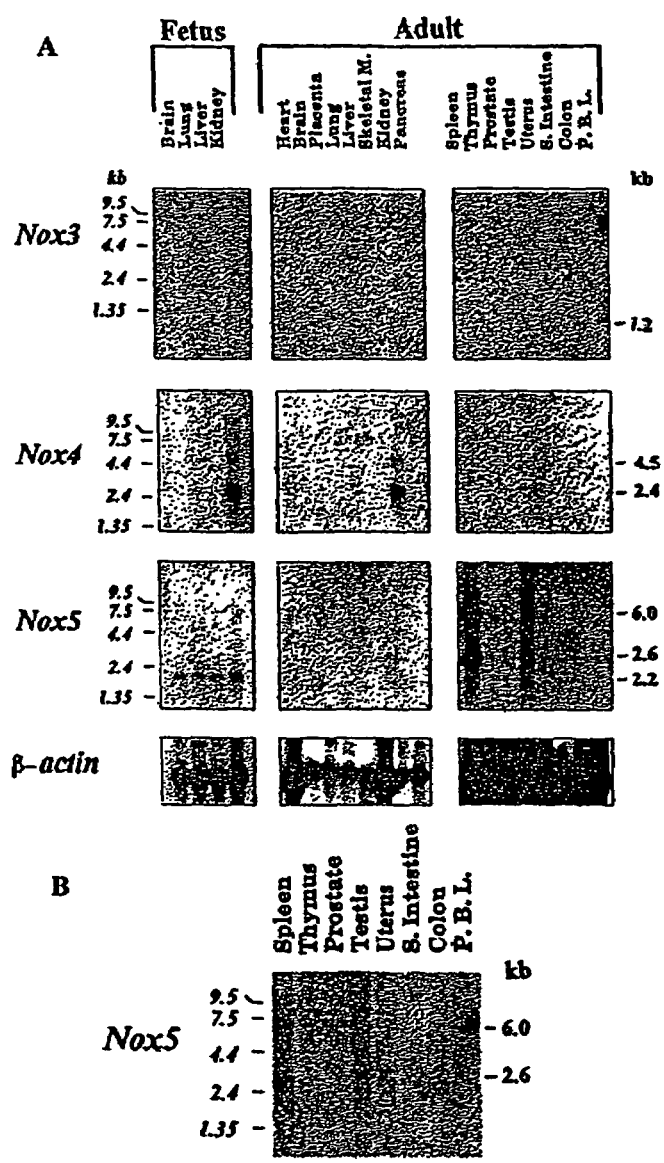
FIG. 4(*a-b*) depicts tissue expression of Nox 3, Nox 4, and Nox 5 measured by Northern Blot analysis.

The predominant Nox 4 2.4 kb message, which corresponds to the size expected for the full-length Nox 4 transcript, is highly expressed in adult as well as fetal kidney (FIG. 4A). An additional weak Nox 4 band was also detected at 4.5 kilobases (kb) in fetal and adult kidney (FIG. 4A). It is particularly expressed at the site of erythropoietin production in the kidney. RT-PCR confirmed kidney expression and also revealed expression of Nox 4 in all fetal tissues tested as well as in several adult tissues including pancreas, placenta, ovary, testis and skeletal muscle.

EXAMPLE 3

Sequence Analysis and Cloning of the cDNA for Human Nox 5

The Blast search using Nox 3 (SEQ ID NO:6) as a query sequence also identified homology with fragments of genomic clone RP11-809H16 of chromosome 15, these fragments are SEQ ID NOS: 32, 33 and 34. These clones exhibit 46 to 50% identity to Nox 3 within three exons. 5'- and 3'-RACE were carried out using human fetal kidney marathon-ready cDNA (Clontech, Palo Alto, Calif.), using the following four primers which were designed based on the genomic sequence: SEQ ID NO:15, 5'-CTCATTGTCA-CACTCCTCGACAGC-3'; SEQ ID NO:16, 5'-TGGGTCT-GATGCCTTGAAGGACTC-3' (for nested PCR); 3'-RACE: SEQ ID NO:17, 5'-ATCAAGCGGCCCCCTTTTTTTCAC-3'; SEQ ID NO:18, 5'-CTGAACATCCCCACCAT-TGCTCGC-3' (for nested PCR). PCR parameters were 95° C. for 30s, 62° C. or 65° C. for 20s, 72° C. for 45s, 25-35 cycles as indicated after denaturing for 1.5 minutes at 95° C. PCR products were purified with a QIAquick PCR purification kit or a gel purification kit (QIAGEN, Valencia, Calif.). Primers were designed to subclone the full-length cDNA and the correct sequence was confirmed by ABI 3777 automated sequencing.

Secretion signal sequences were predicted according to web-based SMART program (version 3.1) at EMBL (Heidelberg, Germany). Prediction of open reading frames (ORF) was carried out using the EditSeq program (DNASTAR), and phylogenetic analyses and multiple sequence alignment were carried out using the clustal method using the Megalign program (DNASTAR). Transmembrane alpha helices were predicted using the TMHMM algorithms through the Center for Biological Sequence Analysis (Lyngby, Denmark).

Total RNA was extracted from cell lines with Trizol (Life Technologies, Gaithersburg, Md.) based on the manufacturer's protocol or according to Ishii et al., (1999) for glioma cell lines. RNAs were reverse transcribed into first-strand cDNA with Superscript II (Life Technologies, Gaithersburg, Md.) using oligo-dT according on the method provided by the manufacturer.

Table 4 shows the basic features of the cDNA and the predicted proteins. Like the proteins encoded by gp91 phox (SEQ ID NO:13) and Nox 1 (SEQ ID NO:14), the new sequences for Nox 4 and Nox 5 encode predicted proteins of around 65 kDa, and message sizes are similar in length (2.0-2.2 kb). Nox 3, Nox 4 and Nox 5 show 21-59% identity with gp91phox. Nox 5 forms a unique group, of which it is the only member identified to date, and which is highly divergent from other members of the family. Based on its position in the family tree, Nox 5 may represent the gene which is closest to the primordial Nox.

The alignment of the predicted protein sequences of gp91phox, Nox 1, Nox 3, Nox 4 and Nox 5 is shown in FIG. 2. The molecules are roughly divided into two large domains: an N-terminal cluster of hydrophobic membrane-spanning sequences, and a C-terminal flavoprotein domain. The latter shows weak homology with a number of FAD binding proteins including cytochrome P-450 reductase and ferredoxin-NADP oxidoreductase (Rotrosen et al., 1992; Segal et al., 1992). Within the flavoprotein domain are two segments (indicated in FIG. 2) that show homology with known FAD binding sites in other flavoproteins, and four segments nearer the C-terminus that are homologous to documented pyridine nucleotide binding sites in other proteins. The first of these includes the G-X-G-X-X-P canonical sequence that characterizes pyridine nucleotide binding sites. In all Nox forms, this sequence is followed by an F, which is typical of NADPH- rather than NADH-specific enzymes.

While the N-terminal half of Nox 1, Nox 3, Nox 4, and Nox 5 are all hydrophobic, Nox 5 differs from the others somewhat in the details of predicted transmembrane alpha helices, as illustrated in FIG. 2. Nox 5 does not contain an N-terminal predicted signal peptide, but does contain a predicted transmembrane alpha helix (first hashed box, Nox 5 sequence in FIG. 2). According to the prediction algorithm, the extreme N-terminus of Nox 5 is located on the inside of the membrane, on the same side as the flavoprotein domain. Five additional transmembrane regions are also predicted in these proteins. The most C-terminal of these is strongly predicted in Nox 5. It is necessary to include this transmembrane region in order to generate a model (FIG. 3) which is consistent with known features of gp91phox, particularly a cytosolic facing location of the flavoprotein domain. In this model, known N-linked glycosylation sites in gp91phox are correctly localized to extracellular loops (although these sites are not conserved in other isoforms). In addition, a polybasic loop of gp91phox that binds to the cytosolic regulatory protein p47phox (Biberstine-Kinkade et al., 1999) is localized on the cytosolic face. In general, extracellular loops tend to be highly variable in length and sequence, whereas the transmembrane helices and intracellular loops tend to be more conserved in sequence and length (FIG. 2).

Within the N-terminus are five absolutely conserved histidines (FIG. 2), that are also conserved in all other members of the Nox family of enzymes (data not shown). gp91phox contains two heme groups, the irons of which are each ligated by two histidyl nitrogens (Isogai et al., 1993), and these are thought to reside within the N-terminus (Yu et al., 1998). An additional conserved histidine lies within the FAD-binding region and is therefore not a candidate for heme ligation. Thus, four of the five histidines within the N-terminus probably participate in heme ligation, providing part of the binding sites for two heme groups, as indicated in FIG. 3.

Additionally, located at the extreme N-terminus on the cytosolic side of the membrane of Nox 5 is a highly cationic proline-rich sequence (the Pro-Arg-Rich sequence indicated in FIG. 2 and FIG. 3). This region is thought to serve as a binding sequence for Src-Homology 3 (SH3) domains in another protein. SH3 domains are known to recognize inter- or intra-molecular proline-rich sequences. This is similar to p22phox, a membrane-associated subunit that associates with gp91phox, and contains a C-terminal, proline-rich sequence (Parkos et al., 1988) that serves as a binding site for a SH3 domain in p47phox, one of the cytosolic subunits that regulates the activity of gp91phox. Although not wanting to be bound by the following statement, it is possible that the proline-rich sequence in Nox 5 serves as an internal p22phox, allowing interaction with cytosolic regulatory proteins.

EXAMPLE 4

Tissue Expression of Nox 5 mRNA

Figure 5:
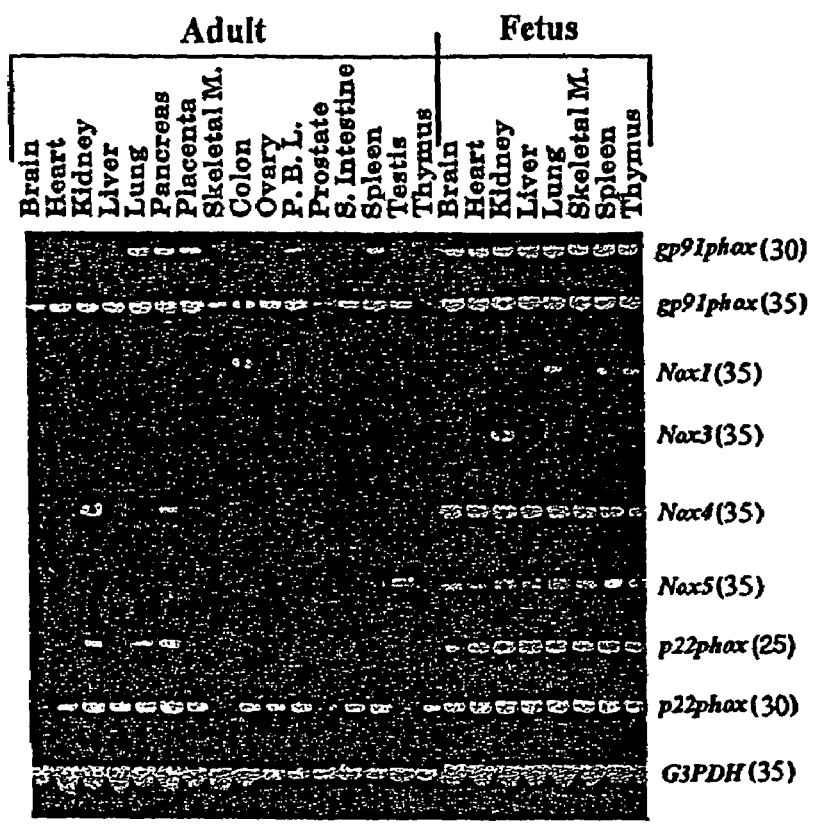
FIG. 5 shows RT-PCR measurement of tissue expression of the Nox family of proteins. RT-PCR was carried out using Nox-specific PCR primers as described herein. The number of cycles was 35, except where indicated (number of cycles in parentheses).

Northern blots probed for Nox 5 using a 3'-portion of the coding region (FIG. 4A) revealed the presence of a 2.2 kb band corresponding in size to the full-length Nox 5 transcript in all fetal tissues tested. This species was also seen in low amounts in adult spleen and testis, along with larger transcripts at 2.6 kb and 6 kb. A probe using a portion of the 3' untranslated region also revealed the presence of the same 2.6 kb and 6 kb bands (FIG. 4B). Thus, these larger bands are larger transcripts derived from the same gene. RT-PCR confirmed expression of Nox 5 in testis and spleen, and also revealed weak expression in ovary, placenta, and pancreas (FIG. 5).

EXAMPLE 5

Real Time RT-PCR of Nox 4 and Nox 5

G3PDH was used as a control. The G3PDH PCR product was purified using a QIAquick PCR purification kit (QIAGEN, Valencia, Calif.) and quantified using absorbance at 260 nm using a BECKMAN DU640B spectrophotometer. The standard curve for G3PDH was constructed using 10-fold serial dilutions of a known concentration of G3PDH PCR product in distilled water. Real time PCR amplification was carried out using a LightCycler (Roche Molecular Biochemicals, Indianapolis, Ind.) in a PCR reaction containing 0.2 µM of each primer, 1: 84,000 SYBR Green I (Molecular Probes, Eugene, Oreg.) and Advantage 2 Polymerase Mix (Clontech, Polo Alto, Calif.). Amplification was carried out for 36 cycles of denaturation (95° C., 0s, ramp rate 20°/s), annealing (65° C., 5s, ramp rate 20/s) and extension (72° C., 30s ramp rate 20° C./s). Fluorescence was monitored at the end of each extension phase. Quantitation and melting curve were analyzed with the LightCycler software. RT-PCR confirmed kidney expression and also revealed expression of Nox 4 in all fetal tissues tested as well as in several adult tissues including pancreas, placenta, ovary, testis and skeletal muscle. (See FIG. 5) The ratio of copies of unknown to standard G3PDH was then calculated and is reported in FIG. 6C. RT-PCR also confirmed expression of Nox 5 in testis and spleen, and revealed weak expression in ovary, placenta, and pancreas (FIG. 5). The data indicate that expression patterns of Nox family members are tissue specific, and do not correspond to the expression of gp91phox.

EXAMPLE 6

Northern Blotting of Nox 4 and Nox 5

The Human Fetal and Adult Multiple Tissue Northern Blot (Clontech, Palo Alto, Calif.) was hybridized with $^{32}$P-random primer-labeled Nox 4, or Nox 5 probe according to the manufacturer's instructions. The probes were prepared by PCR with primers for Nox 4: SEQ ID NO:7 and SEQ ID NO:8; and primers for Nox 5: SEQ ID NO:19, 5'-CTGAACATC-CCCACCATTGCTCGC-3' and SEQ ID NO: 20, 5'-GAAGCCGAACTTCTCACAATGGCC-3'. The PCR products represent coding sequences corresponding to amino acids 11-294 (Nox 4), or 278-557 (Nox 5). Because the Nox 5 transcript sizes differ between fetal and adult northern blots, a 420 bp PCR product of the Nox 5 3'-untranslated region amplified by primers (SEQ ID NO: 21 5'-CCTCACCTCTC-CAAGCTCTGCCCC-3' and SEQ ID NO: 22 5'-TTGAA-CAATTTTATAAGATGCCGG-3') was also used to hybridize Northern Blots.

The predominant Nox 4 2.4 kb message, which corresponds to the size expected for the full-length Nox 4 transcript, is highly expressed in adult as well as fetal kidney (FIG. 4A), confirming recent reports (Kikuchi et al., 2000; Geiszt et al., 2000; Shiose et al., 2000). An additional weak Nox 4 band was also detected at 4.5 kilobases (kb) in fetal and adult kidney (FIG. 4A). Northern blots probed for Nox 5 (FIG. 4A) revealed the presence of a 2.2 kb band corresponding in size to the full-length Nox 5 transcript in all fetal tissues tested. This species was also seen in low amounts in adult spleen and testis, along with larger transcripts at 2.6 kb and 6 kb. A probe using a portion of the 3' untranslated region also revealed the presence of the same 2.6 kb and 6 kb bands (FIG. 4B). Thus, these larger bands are larger transcripts derived from the same gene.

EXAMPLE 7

Transfection of NIH3T3 Cells with SEQ ID NO:1 or SEQ ID NO:3

The nucleotide sequence SEQ ID NO:1 or SEQ ID NO:3 encoding for production of the Nox 4 protein (SEQ ID NO:2) or the Nox 5 protein (SEQ ID NO:4), respectively, is subcloned into the Not1 site of the pEF-PAC vector (obtained from Mary Dinauer, Indiana University Medical School, Indianapolis, Ind.) which has a puromycin resistance gene. Transfection is carried out as described in Sambrook et al., Molecular Cloning, A Laboratory Manual, Volumes 1-3, 2nd edition, Cold Spring Harbor Laboratory Press, N.Y., 1989. The SEQ ID NO:1 in pEF-PAC and the empty vector are separately transfected into NIH 3T3 cells using Fugene 6 (Boeringer Mannheim).

$10^5$ to $10^3$ cells stably transfected separately with human Nox 4 gene SEQ ID NO:1, with human Nox 5 gene SEQ ID NO:3, and with empty vector are prepared in 0.3% warm (40° C.) agar solution containing DMEM and 10% calf serum. Cells are distributed onto a hardened 0.6% agar plate prepared with DMEM and 10% calf serum. After three weeks in culture (37° C., 5% $CO_2$) colony formation is observed by microscopy.

About 2×10⁶ cells maintained in DMEM containing 10% calf serum are transfected with 10 µg of DNA. After 2 days, cells are split and selected in the same medium containing 1 mg/ml puromycin. Colonies that survive in selection media for 10 to 14 days are subcultured continuously in the presence of puromycin.

Cells which are stably transfected with the empty vector and cultured in soft agar for 3 weeks as above do not display anchorage independent growth. In contrast, NIH 3T3 cells which are stably transfected with the Nox 4 (SEQ ID NO:1) or with the Nox 5 gene (SEQ ID NO:3) cultured for 3 weeks in soft agar demonstrate anchorage independent growth of colonies. Transfected cells exhibit a transformed-like morphology, similar to that seen with (V12) Ras-transfected cells, characterized by long spindle-like cells.

EXAMPLE 8

Expression of Nox 4 (SEQ ID NO:1) or Nox 5 (SEQ ID NO:3) in Transfected NIH3T3 Cells To verify the expression of Nox 4 mRNA or Nox 5 mRNA after transfection, RT-PCR and Northern blotting are performed. Total RNAs are prepared from 10⁶ cells using the High Pure RNA Isolation Kit (Boeringer Mannheim) or Rneasy kit (Qiagen). cDNAs for each colony are prepared from 1-2 µg of total RNA using Advantage RT-PCR Kit (ClonTech). PCR amplification is performed using primers, SEQ ID NO: 23 and SEQ ID NO:24. For Northern blotting, 10-20 µg of total RNA is separated on a 1% agarose formaldehyde gel and transferred to a nylon filter. After ultraviolet (UV) cross-linking, filters are used for Northern blotting assay as described in Example 6. Colonies expressing large amounts of Nox 4 mRNA or Nox 5 mRNA are chosen for further analysis.

EXAMPLE 9

NADPH-Dependent Superoxide Generation Assay

In one embodiment of the present invention, NIH 3T3 cells stably transfected with the human Nox 4 gene (SEQ ID NO:1) or human Nox 5 gene (SEQ ID NO:3) are analyzed for superoxide generation using the lucigenin (Bis-N-methylacridinium luminescence assay (Sigma, St. Louis, Mo., Li et al. (1998) J. Biol. Chem. 273, 2015-2023). Cells are washed with cold HANKS' solution and homogenized on ice in HANKS' buffer containing 15% sucrose using a Dounce homogenizer. Cell lysates are frozen immediately in a dry ice/ethanol bath. For the assay, 30 µg of cell lysate is mixed with 200 µM NADPH and 500 µM lucigenin. Luminescence is monitored using a LumiCounter (Packard) at three successive one minute intervals and the highest value was used for comparison. Protein concentration is determined by the Bradford method.

Superoxide generation is monitored in lysates from some of the stably transfected cell lines and is compared with superoxide generation by the untransfected NIH 3T3 cell lysates. The luminescent signal is inhibited by superoxide dismutase and the general flavoprotein inhibitor diphenylene iodonium, but is unaffected by added recombinant human p47phox, p67phox and Rac1 (GTP-γS), which are essential cytosolic factors for the phagocyte respiratory-burst oxidase.

In an alternate and preferred embodiment of the present invention, cells that are stably transfected with Nox 4 (YA28), Nox 5 (YA28) or with empty vector (NEF2) are grown in 10 cm tissue culture plates in medium containing DMEM, 10% calf serum, 100 units/ml penicillin, 100 µg/ml streptomycin, and 1 µg/ml puromycin to approximately 80% confluency. Cells (five tissue culture plates of each cell type) are washed briefly with 5 ml phosphate buffered saline (PBS) then dissociated from the plates with PBS containing 5 mM EDTA. Cells are pelleted by centrifuging briefly at 1000×g.

To permeabilize the cells, freeze thaw lysis is carried out and this is followed by passage of the cell material through a small bore needle. The supernatant is removed and the cells are frozen on dry ice for 15 minutes. After cells are thawed, 200 µl lysis buffer (HANKS' Buffered Salt Solution—HBBS) containing a mixture of protease inhibitors from Sigma (Catalog no. P2714) is added. Cells on ice are passed through an 18 gauge needle 10 times and 200 µl of HBSS buffer containing 34% sucrose was added to yield a final concentration of 17% sucrose. Sucrose appeared to enhance stability upon storage. The combination of freeze-thawing and passage through a needle results in lysis of essentially all of the cells, and this material is referred to as the cell lysate.

The cell lysates are assayed for protein concentration using the BioRad protein assay system. Cell lysates are assayed for NADPH-dependent chemiluminescence by combining HBSS buffer, arachidonic acid, and 0.01-1 µg protein in assay plates (96 well plastic plates). The reaction is initiated by adding 1.5 mM NADPH and 75 µM lucigenin to the assay mix to give a final concentration of 200 µM NADPH and 10 µM lucigenin, and the chemiluminescence is monitored immediately. The final assay volume as 150 µl. The optimal arachidonic acid concentration is between 50-100 µM. A Packard Lumicount luminometer is used to measure chemiluminescence of the reaction between lucigenin and superoxide at 37° C. The plate is monitored continuously for 60 minutes and the maximal relative luminescence unit (RLU) value for each sample is used for the graph.

The presence of NaCl or KCl within a concentration range of 50-150 µM is important for optimal activity. $MgCl_2$ (1-5 mM) further enhanced activity by about 2-fold. This cell-free assay for Nox 4 NADPH-oxidase activity and the cell-free assay for Nox 5 NADPH-oxidase are useful for screening modulators (inhibitors or stimulators) of the Nox 4 enzyme and Nox 5 enzyme. The assay may also be used to detect Nox NADPH-oxidase activity in general and to screen for modulators (inhibitors or stimulators) of the Nox family of enzymes.

EXAMPLE 10

Nitro Blue Tetrazolium Reduction by Superoxide Generated by NIH 3T3 Cells Transfected with the Nox 4 cDNA (SEQ ID NO:1) or the Nox 5 cDNA (SEQ ID NO:3)

Superoxide generation by intact cells is monitored by using superoxide dismutase-sensitive reduction of nitroblue tetrazolium. NEF2 (vector alone control), YA26 (Nox 4 (SEQ ID NO:1)-transfected), YA26 (Nox 5 (SEQ ID NO:3)-transfected), YA28 (Nox 4 (SEQ ID NO:1)-transfected) and YA28 (Nox 5 (SEQ ID NO:3)-transfected) cells are plated in six well plates at 500,000 cells per well. About 24 hours later, medium is removed from cells and the cells are washed once with 1 mL Hanks solution (Sigma, St. Louis, Mo.). About 1 mL of filtered 0.25% Nitro blue tetrazolium (NBT, Sigma) is added in Hanks without or with 600 units of superoxide dismutase (Sigma) and cells are incubated at 37° C. in the presence of 5% $CO_2$. After 8 minutes the cells are scraped and pelleted at more than 10,000 g. The pellet is re-suspended in 1 mL of pyridine (Sigma) and heated for 10 minutes at 100° C. to solubilize the reduced NBT. The concentration of reduced NBT is determined by measuring the absorbance at 510 nm, using an extinction coefficient of 11,000 $M^{-1}$ $cm^{-1}$. Some wells are untreated and used to determine cell number. Because superoxide dismutase is not likely to penetrate cells, superoxide must be generated extracellularly. The amount of superoxide generated by these cells is about 5-10% of that generated by activated human neutrophils.

EXAMPLE 11

Modification of Intracellular Components in Nox 4 and Nox 5 Transfected Cells

To test whether superoxide generated by Nox 4 or Nox 5 can affect intracellular targets, aconitase activity in control and Nox-transfected cell lines is monitored using a method as described in Suh et al. (1999) *Nature* 401, 79-82. Aconitase contains a four-iron-sulphur cluster that is highly susceptible to modification by superoxide, resulting in a loss of activity, and has been used as a reporter of intra-cellular superoxide generation. Acotinase activity is determined as described in Gardner et al. (1995) *J. Biol. Chem.* 270, 13399-13405. Acotinase activity is significantly diminished in the Nox-transfected cell lines designated YA26, and YA28 as compared to the transfected control.

Approximately 50% of the aconitase in these cells is mitochondrial, based on differential centrifugation, and the cytosolic and mitochondrial forms were both affected. Control cytosolic and mitochondrial enzymes that do not contain iron-sulfur centers are not affected. Superoxide generated in Nox 4-transfected cells and Nox 5-transfected cells is therefore capable of reacting with and modifying intracellular components.

EXAMPLE 12

Tumor Generation in Nude Mice Receiving Cells Transfected with the Human Nox 4 cDNA (SEQ ID NO:1) or the Human Nox 5 cDNA (SEQ ID NO:3)

About $2\times10^6$ NIH 3T3 cells (either Nox 4-transfected with SEQ ID NO:1, Nox 5-transfected with SEQ ID NO:3, or cells transfected using empty vector) are injected subdermally into the lateral aspect of the neck of 4-5 week old nude mice. Three to six mice are injected for each of three Nox 4-transfected cell lines, each of the Nox 5-transfected cell lines, and 3 mice are injected with the cells transfected with empty vector (control). After 2 to 3 weeks, mice are sacrificed. The tumors are fixed in 10% formalin and characterized by histological analysis.

In another study, 15 mice are injected with Nox 4-transfected NIH 3T3 cells. Of the 15 mice injected, 14 show large tumors within 17 days of injection, and tumors show expression of Nox 4 mRNA.

In another study, 15 mice are injected with Nox 5-transfected NIH 3T3 cells. Of the 15 mice injected, 14 show large tumors within 17 days of injection, and tumors show expression of Nox 5 mRNA.

EXAMPLE 13

Demonstration of the Role of Nox 4 and Nox 5 in Non-Cancerous Growth

A role for Nox 4 and Nox 5 in normal growth is demonstrated in rat aortic vascular smooth-muscle cells by using antisense to Nox 4 or Nox 5. Transfection with the antisense DNA results in a decrease in both superoxide generation and serum-dependent growth. Nox 4 and Nox 5 are therefore implicated in normal growth in this cell type.

EXAMPLE 14

Expression of Human Nox 4 Protein (SEQ ID NO:2) and Human Nox 5 Protein (SEQ ID NO: 4) in a Baculovirus Expression System SEQ ID NO:2 and SEQ ID NO:4 are also expressed in insect cells using recombinant baculovirus. To establish the Nox 4 and Nox 5 expressing virus systems, the Nox 4 gene (SEQ ID NO:1) or the Nox 5 gene (SEQ ID NO:5) is initially cloned separately into the pBacPAK8 vector (Clontech, Palo Alto, Calif.) and recombinant baculovirus is constructed using standard methods according to manufacturer's protocols. Briefly, PCR amplified Nox 4 DNA or Nox 5 DNA is cloned into the KpnI and EcoRI site of the vector. Primers used for PCR amplification are SEQ ID NOs:21, 22, 23 and 24. Sf9 insect cells ($2\times10^6$ cells) are infected with 0.5 mg of linearized baculovirus DNA sold under the trademark BACULOGOLD® (PharMingen, San Diego, Calif.) and 5 mg pBacPAC8 Nox 4 using Transfection Buffers A and B (PharMingen, San Diego, Calif.). After 5 days, the supernatants containing recombinant viruses are harvested and amplified by infecting fresh sf9 cells for 7 days. Amplification is carried out three times and the presence of the recombinant viruses containing Nox 4 DNA or Nox 5 DNA is confirmed by PCR using the same primers. After three times amplification of viruses, plaque purification are carried out to obtain the high titer viruses. Approximately $2\times10^8$ sf9 cells in agar plates are infected for 5 days with serial dilutions of virus and are dyed with neutral red for easy detection of virus plaques. Selected virus plaques are extracted and the presence of the human Nox 4 DNA or human Nox 5 DNA is confirmed again by PCR.

EXAMPLE 15

Antibodies to Human Nox 4 (SEQ ID NO:2) and Human Nox 5 (SEQ ID NO:4)

Polyclonal antibodies are raised separately in rabbits against human Nox 4 (SEQ ID NO:2) or human Nox 5 (SEQ ID NO: 4). Proteins are separately conjugated to keyhole limpet hemocyanin (KLH) using glutaraldehyde.

Antigens are injected into different rabbits initially in complete Freund's adjuvant, and are boosted 4 times with antigen in incomplete Freund's adjuvant at intervals of every three weeks. Approximately 0.5 mg to 1 mg of peptide is administered at each injection. Blood is drawn 1 week after each boost and a terminal bleed is carried out 2 weeks after the final boost. Anti Nox 4 and anti Nox 5 antibodies are purified on affinity columns to which are bound Nox 4 or Nox 5 using techniques known to one of ordinary skill in the art. Unbound protein is washed away with 20 ml of buffer. Elution of the antibodies from the gel was performed with 6 ml of elution buffer (100 mM glycine/HCl, pH 2.5, 200 mM NaCl, and 0.5% Triton X-100). The eluate is then neutralized by adding 0.9 ml of 1 M Tris/HCl, pH 8.0.

The detection of antigens is performed using an enhanced chemiluminescence kit (Amersham, Buckinghamshire, UK). The affinity purified antibodies to Nox 4 or to Nox 5 are used at a dilution of 1:1000 in a Western blot in which a total of 10 µg of protein is added to each lane.

EXAMPLE 16

Figure 7:
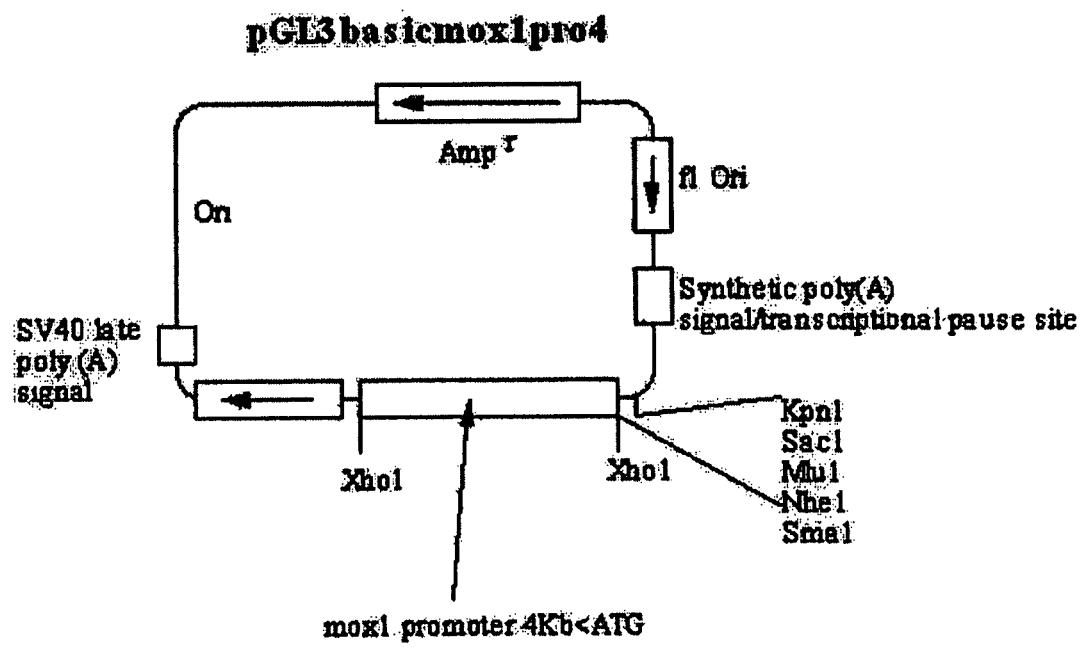
FIG. 7 depicts the creation of a promoter-reporter construct for Nox 1.

Construction of a Reporter Construct for Nox-1 pGL3-basic (Promega, Madison, Wis.) was used as the parent vector. The pGL3-basic vector lacks eukaryotic promoter and enhancer sequences, allowing for maximum flexibility in cloning putative regulatory sequences. Expression of luciferase activity in cells transfected with this plasmid depends on insertion and proper orientation of a functional promoter upstream from luc+. Potential enhancer elements can also be inserted upstream of the promoter or in the BamH I or Sal I sites downstream of the luc+ gene. Primers SEQ ID NO: 25, 5'GCTACTCGAGTGTGCCAATTTCACCTG-GCAT-3' and SEQ ID NO:26, 5'-AACTCTCGAGTGTCAA-GAGGTGGTTTGGAGC-3' were used along with genomic DNA to obtain the promoter region of Nox 1 (SEQ ID NO:5) flanked by Xho restriction sites. The restriction sites were then used to insert the Nox 1 promoter region into the pGL3 plasmid. (See FIG. 7). Successful transfection was determined by the activity of luciferase which was measured using a luminometer.

EXAMPLE 17

Use of the Reporter Construct as an Assay

The construct from Example 16 is stably transfected into human Caco-2 or HT-29 cells. Transfection is carried out as described in Sambrook et al., Molecular Cloning, A Laboratory Manual, Volumes 1-3, 2nd edition, Cold Spring Harbor Laboratory Press, N.Y., 1989. The SEQ ID NO:5 in pEF-PAC and the empty vector are separately transfected into Caco-2 cells using Fugene 6 (Boeringer Mannheim). $10^5$ to $10^3$ cells stably transfected with human Nox 1 promoter gene SEQ ID NO:5 and with empty vector are prepared in 0.3% warm (40° C.) agar solution containing DMEM and 10% calf serum. Cells are distributed onto a hardened 0.6% agar plate prepared with DMEM and 10% calf serum. After three weeks in culture (37° C., 5% $CO_2$) colony formation is observed by microscopy. About $2\times10^6$ cells maintained in DMEM containing 10% calf serum are transfected with 10 µg of DNA. After 2 days, cells are split and selected in the same medium containing 1 mg/ml puromycin. Colonies that survive in selection media for 10 to 14 days are subcultured continuously in the presence of puromycin.

The colonies are used as a screening assay by adding compounds to the media suspected of effecting the expression of ROI. Measurement of the luciferase output indicates whether a compound enhanced or inhibited the induction of the Nox 1 gene and facilitates the development of drugs based on a compound's cellular effects.

EXAMPLE 18

Expression of Nox 3, Nox 4, and Nox 5 mRNA in Cancer Cells

Figure 6A:
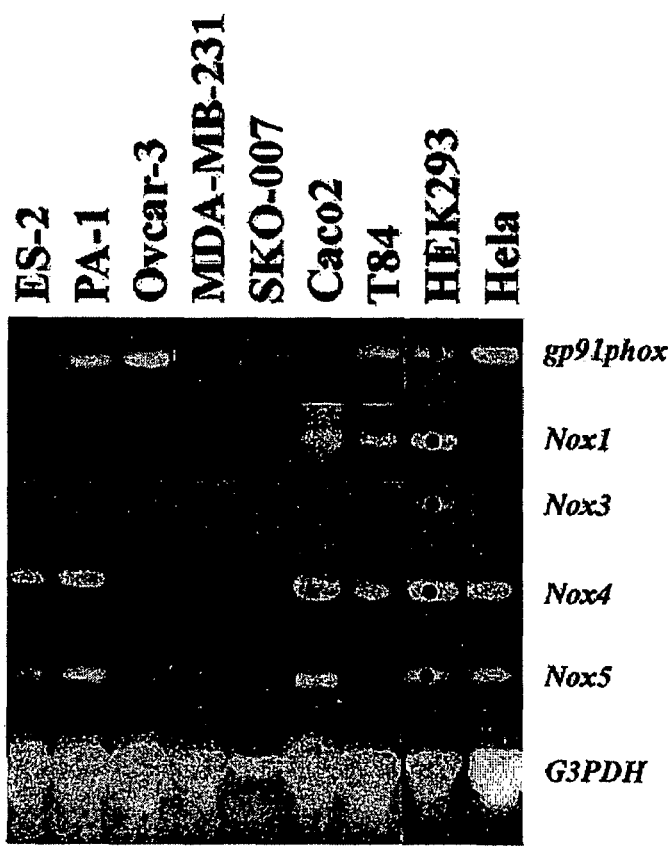
FIG. 6 (*a-b*) depicts expression of Nox isoforms in tumor or transformed cell lines.
FIG. 6*c* shows the ratio of expression of gp91phox, Nox 4, and Nox 5 compared with glyceraldehyde-3-phosphate dehydrogenase (G3PDH), obtained from real time PCR results.
Figure 6B:
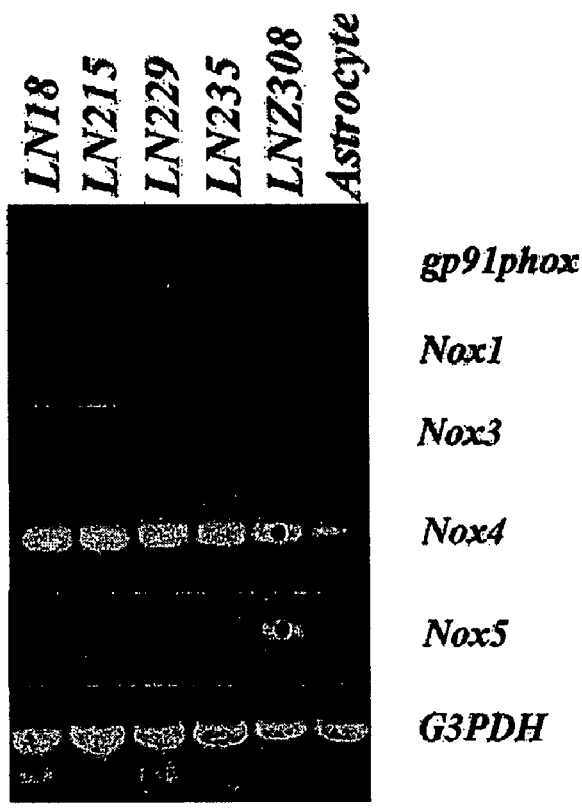
Figure 6C:
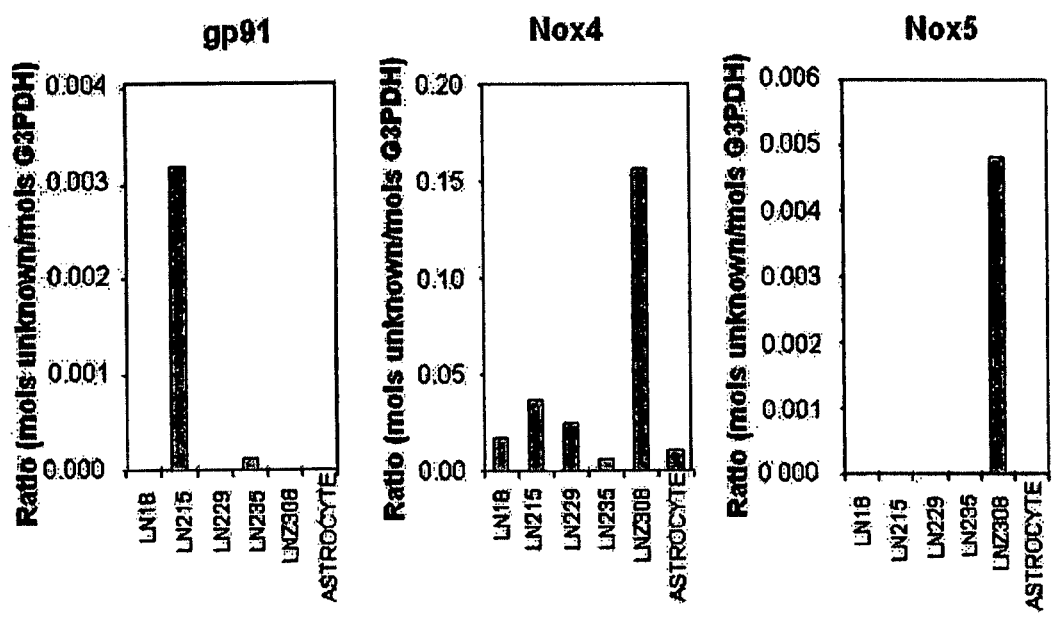

Many cancer cells overproduce reactive oxygen specis (Szatrowski and Nathan, 1991), and this may be causative in the transformed phenotype (Suh et al., 1999). The expression of Nox 1-5 was investigated in a variety of human tumor and other cell lines, to determine if these enzymes might account for reactive oxygen generation seen in some tumors. Expression of Nox family members in human cancers. RT-PCR was carried out as in FIG. 5. FIG. 6A shows Nox expression in the following cell lines: ES-2 (ovarian clear cell carcinoma), PA-1 (ovarian teratocarcinoma), Ovcar-3 (ovarian adenocarcinoma), MDA-MB-231 (mammary adenocarcinoma), SKO-007 (plasmacytoma), Caco-2 (colon carcinoma), T84 (colon carcinoma), HEK293 (embryonic kidney transformed with adenovirus), and Hela. (cervical adenocarcinoma). FIG. 6B show Nox expression in five cell lines derived from human glioblastomas, as well as from human astrocyte primary cultures. FIG. 6C shows the ratio of expression of gp91phox, Nox 4 and Nox 5 compared with G3PDH, obtained from real time PCR results.

As shown in FIGS. 6A and 6B, Nox isoforms were expressed in 12 out of the 14 tumor or transformed cell lines examined. Nox 1 is expressed in two colon cancer lines, Caco-2 and T-84, as well as in the transformed cell line HEK293, and to a lesser extent in Hela cells. Nox 4 was seen in 11 of these cell lines, while Nox 5 was seen in 7. gp91phox was also expressed in more than half of the cell lines. The identity of the mRNAs was confirmed by sequencing as indicated in FIGS. 5, 6A and B.

In live brain tumor cell lines derived from human glioblastomas, Nox 4 was always expressed, along with variable expression of Nox 5 and gp91phox (FIG. 6B). Real time PCR revealed that the ratio of expression of Nox to G3PDH varied significantly in the various tumor cell lines compared with primary human astrocytes (FIG. 6C). Although the cellular origin of glioblastomas has not been definitively established, this cancer type is thought by many workers to have arisen from the astrocytic lineage.

The expression of Nox forms in cancer and transformed cell lines did not correlate strictly with the expression in normal tissue, indicating that expression of Nox isoforms is sometimes altered in cancer cells. Thus, aberrant expression or regulation of Nox isoforms could account for the increased reactive oxygen generation seen in some cancer cells.

All patents, publications and abstracts cited above are incorporated herein by reference in their entirety. U.S. provisional patent applications Ser. Nos. 60/249,305, 60/251,364, 60/289,172, 60/289,537 are hereby incorporated by reference in their entirety. It should be understood that the foregoing relates only to preferred embodiments of the present invention and that numerous modifications or alterations may be made therein without departing from the spirit and the scope of the present invention as defined in the following claims.

We claim:

1. An isolated antibody, wherein the antibody specifically binds a polypeptide consisting of the amino acid sequence of SEQ ID NO: 4, a fragment of the amino acid sequence of SEQ ID NO: 4 comprising the flavoprotein domain, or a substitution of SEQ ID NO: 4 of less than 1% of the amino acid sequence comprising the flavoprotein domain.

2. The isolated antibody of claim 1, wherein the antibody specifically binds the amino acid sequence set forth as SEQ ID NO:4.

3. The isolated antibody of claim 1, wherein the antibody is a monoclonal antibody.

4. The isolated antibody of claim 1, wherein the antibody is a polyclonal antibody.

5. The isolated antibody of claim 1, wherein the antibody is labeled.

6. The isolated antibody of claim 1, wherein the label is a radiolabel, a dye, a magnetic particle, biotin, avidin, a fluorescent molecule, a chemiluminescent molecule, ferritin, a cytotoxin or colloidal gold.

7. A method for detecting a protein, comprising
contacting a sample with the antibody of claim 1; and
detecting binding of the antibody to a protein comprising the amino acid sequence of SEQ ID NO: 4, a fragment of SEQ ID NO: 4 comprising the flavoprotein domain, or a substitution of SEQ ID NO: 4 of less than 1% of the amino acid sequence comprising the flavoprotein domain wherein the protein is capable of superoxide production, thereby detecting the protein.

8. The method of claim 7, wherein the sample is a cell, cellular extract, tissue, tissue extract, biopsy or biological fluid.

9. The method of claim 7, wherein the antibody is a polyclonal antibody.

10. The method of claim 7, wherein the antibody is a monoclonal antibody.

11. The method of claim 7, wherein the antibody is labeled.

12. The method of claim 11, wherein the antibody is labeled with a dye, a magnetic particle, biotin, avidin, a fluorescent molecule, a chemiluminescent molecule, ferritin, or colloidal gold.

* * * * *

UNITED STATES PATENT AND TRADEMARK OFFICE
CERTIFICATE OF CORRECTION

PATENT NO. : 7,524,936 B2
APPLICATION NO. : 11/712222
DATED : April 28, 2009
INVENTOR(S) : J. David Lambeth and Guangjie Chang Page 1 of 1

It is certified that error appears in the above-identified patent and that said Letters Patent is hereby corrected as shown below:

Col. 1, replace lines 17 to 21 as follows:

--ACKNOWLEDGEMENT

This invention was made with government support under Grants HL38206, HL58000, and CA084138 awarded by the National Institutes of Health. The government has certain rights in the invention.--

Signed and Sealed this
Tenth Day of April, 2012

David J. Kappos
*Director of the United States Patent and Trademark Office*